United States Patent
Memita et al.

(10) Patent No.: US 6,939,980 B2
(45) Date of Patent: Sep. 6, 2005

(54) PROCESS FOR PRODUCING ESTER

(75) Inventors: Michimasa Memita, Amagasaki (JP); Keiji Hirao, Kobe (JP)

(73) Assignee: NOF Corporation, Tokyo (JP)

( * ) Notice: Subject to any disclaimer, the term of this patent is extended or adjusted under 35 U.S.C. 154(b) by 102 days.

(21) Appl. No.: 10/380,662

(22) PCT Filed: Sep. 10, 2001

(86) PCT No.: PCT/JP01/07861

§ 371 (c)(1),
(2), (4) Date: Mar. 11, 2003

(87) PCT Pub. No.: WO02/22548

PCT Pub. Date: Mar. 21, 2002

(65) Prior Publication Data

US 2003/0187292 A1 Oct. 2, 2003

(30) Foreign Application Priority Data

Sep. 11, 2000 (JP) ........................................ 2000-275623

(51) Int. Cl.[7] .......................... C07C 51/00; C07C 1/00; C07C 3/00; C07C 67/02
(52) U.S. Cl. ...................... 554/170; 554/172; 560/263; 560/265
(58) Field of Search ................................ 554/170, 172; 560/263, 265

(56) References Cited

U.S. PATENT DOCUMENTS

| | | | | |
|---|---|---|---|---|
| 2,588,194 A | * | 3/1952 | Arundale et al. | 260/485 |
| 4,314,071 A | * | 2/1982 | Babler | 560/127 |
| 4,868,324 A | * | 9/1989 | Stautzenberger et al. | 560/78 |
| 5,466,719 A | * | 11/1995 | Jakobson et al. | 514/785 |
| 5,856,523 A | * | 1/1999 | Miao et al. | 549/274 |
| 6,423,856 B1 | * | 7/2002 | Springer et al. | 554/173 |

FOREIGN PATENT DOCUMENTS

| | | | |
|---|---|---|---|
| GB | 951937 | * | 3/1964 |
| JP | 55-147243 A | | 11/1980 |
| JP | 1-207258 A | | 8/1989 |
| JP | 6-271881 A | | 9/1994 |
| JP | 7-118681 A | | 5/1995 |
| JP | 9-13063 A | | 1/1997 |
| JP | 9-316479 A | | 12/1997 |
| JP | 11-80766 A | | 3/1999 |
| JP | 11-321116 A | | 11/1999 |
| JP | 11-322697 A | | 11/1999 |

OTHER PUBLICATIONS

The Merck Index, 13th ed., Merck & Co., Inc., © 2001, p. 7389.*

* cited by examiner

Primary Examiner—James O. Wilson
Assistant Examiner—Zachary C. Tucker
(74) Attorney, Agent, or Firm—The Webb Law Firm, P.C.

(57) ABSTRACT

A method for producing an ester comprising the steps of reacting an alcohol with a carboxylic acid to obtain a crude esterfied product, adding 5 to 100 parts by weight of a hydrocarbon solvent with respect to 100 parts by weight of the crude esterified product and performing neutralization with an alkali aqueous solution. An alcohol solvent can be added, if necessary. Thus, a method for producing an ester is provided in which a high-quality ester is obtained at a high yield.

6 Claims, No Drawings

PROCESS FOR PRODUCING ESTER

This application was filed under 35 U.S.C. 371, and is the U.S. National Stage of PCT/JP01/07861, filed 10 Sep. 2001.

BACKGROUND OF THE INVENTION

1. Field of the Invention

The present invention relates to a method for producing an ester. More specifically, the present invention relates to a method for producing an ester that can provide a high-quality and heat-resistant ester with high yield.

2. Description of the Prior Art

Esters are used in a wide range of fields such as cosmetics, pharmaceutical preparations, foods, electronic equipment, printing, and lubricants, to mention a few. In recent years, with technological development in these fields, there is a large demand for high-quality esters. For example, for ester waxes having a high melting point used in lubricants for toner, sharp melting characteristics and high heat resistance are required. Therefore, for this use, there is a demand for an ester having a small content of low volatile substances, raw material alcohols, raw material carboxylic acids, esters containing a hydroxyl group or the like, and which exhibits a small weight loss at high temperatures. For esters used for refrigerating machine oils, such properties as high electric insulation and a high heat resistance are required. In order o obtain such properties, it is necessary that very low levels of contaminants or conductive impurities are present and the acid value and hydroxyl value of the esters are low, in order that the hydrolytic stability and heat stability at high temperatures of the esters are excellent.

Esters can be produced by a reaction between an alcohol and a carboxylic acid, as well known. In general, this reaction is carried out with an excessive amount of carboxylic acid, and an ester can be obtained from the resultant crude esterified product by a process of removing the excessive carboxylic acid by one of the following processes alone or by combining these processes: a process of topping under reduced pressure; a process of neutralization with an alkaline aqueous solution; and a process of adsorption treatment that removes the carboxylic acid by adsorption. However, if the process of topping under reduced pressure is employed alone, the acid value is insufficiently reduced, and furthermore, this process may lead to heat deterioration because of exposure to high temperature, which may impair the quality.

Therefore, neutralization with an alkali aqueous solution is commonly employed after an esterification reaction, as disclosed in the examples of Japanese Laid-Open Patent Publication Nos. 6-271881, 7-118681 and 9-316479. However, neutralization has the problems that a produced ester is incorporated into an alkaline aqueous layer, which results in poor separation of the layers. In particular, in the case of a highly viscous ester or a high melting point ester derived from straight and long chain saturated monocarboxylic acid, the layers are poorly separated or an emulsified state occurs, so that the acid value is not sufficiently reduced or the yield is significantly decreased. To solve these problems, the following processes are employed: a process of adding hot water in which a salt such as sodium chloride or sodium sulfate is dissolved to a mixture to be treated for neutralization so as to increase the difference in the relative density between the ester layer and the alkaline aqueous layer, so that the separation can be improved; and a process of dehydrating a mixture containing an emulsified ester layer and alkaline layer under reduced pressure as it is, and then filtrating the mixture. However, these processes cannot provide sufficient improvement effects, and therefore, cause new problems in that the added salt or a formed carboxylic acid soap (salt of carboxylic acid) remain in the ester, which significantly degrades the quality of the ester.

In addition, purification by performing an absorption treatment with an adsorbent such as activated clay, silica gel, acid clay and a silica-alumina synthetic adsorbent is also used. For example, the examples of Japanese Laid-Open Patent Publication No. 11-80766 describes a purification process by an adsorption treatment, but cannot provide an ester having a satisfactory quality in terms of heat stability and oxidation stability.

SUMMARY OF THE INVENTION

It is an object of the present invention to provide a method for producing an ester that can provide a high-quality ester with high yield. As a result of in-depth research of the inventors of the present invention into the above-described problem, the inventors of the present invention found a method to solve the problem.

The method for producing an ester of the present invention comprises, reacting an alcohol with a carboxylic acid to obtain a crude esterified product; and adding 5 to 100 parts by weight of a hydrocarbon solvent to the crude esterified product with respect to 100 parts by weight of the crude esterified product and performing neutralization using an alkali aqueous solution.

In a preferred embodiment, a solvent that is an alcohol having 1 to 3 carbon atoms is further added to the crude esterified product in addition to the hydrocarbon solvent, in a ratio of 3 to 50 parts by weight with respect to 100 parts by weight of the crude esterified product, and then the neutralization is performed using an alkali aqueous solution.

In a preferred embodiment, the hydrocarbon solvent is at least one selected from the group consisting of toluene, xylene, cyclohexane and normal heptane.

In a preferred embodiment, the melting point of the ester is 50 to 100° C.

In a preferred embodiment, the kinematic viscosity of the ester at 40° C. is 60 to 50,000 $mm^2/s$.

DETAILED DESCRIPTION OF THE PREFERRED EMBODIMENTS

In the method of the present invention, there is no particular limitation regarding the kinds of carboxylic acids used for producing an ester, but carboxylic acid having 5 to 30 carbon atoms can be used preferably. Examples of such carboxylic acids include monocarboxylic acids and polyvalent carboxylic acids. These carboxylic acids can be saturated, unsaturated, linear or branched.

Examples of monocarboxylic acids include valeric acid, isovaleric acid, hexanoic acid, heptanoic acid, 2-methylhexanoic acid, 3-methylhexanoic acid, 4-methylhexanoic acid, 5-methylhexanoic acid, 2,2-dimethylpentanoic acid, 2-ethylpentanoic acid, 3-ethylpentanoic acid, isoheptanoic acid, octanoic acid, 2-ethylhexanoic acid, isooctanoic acid, nonanoic acid, 3,5,5trimethylhexanoic acid, isononanoic acid, decanoic acid, isodecanoic acid, lauric acid, myristic acid, palmitic acid, stearic acid, oleic acid, linoleic acid, linolenic acid, arachidic acid, erucic acid, behenic acid, lignoceric acid, cerotic acid, montanoic acid, melissic acid, and the like.

Examples of polyvalent carboxylic acids include succinic acid, glutaric acid, adipic acid, pimelic acid, suberic acid, azelaic acid, sebacic acid, undecanedioic acid, dodecanedioic acid, tridecanedioic acid, carboxyoctadecanoic acid, carboxymethyloctadecanoic acid, docosanedioic acid, dimer acid, phthalic acid, isophthalic acid, fumaric acid, maleic acid, trimellitic acid, pyromellitic acid, and the like.

In the method of the present invention, there is no particular limitation regarding the kinds of alcohol used for producing esters (hereinafter this alcohol may be referred to as raw material alcohol), but alcohols having 5 to 30 carbon atoms can be used preferably. For the alcohol, any of monovalent alcohols, polyvalent alcohols, and ether compounds that are alkylene oxide adducts of these alcohols can be used.

Examples of monovalent alcohols include pentanol, isopentanol, hexanol, cyclohexanol, heptanol, octanol, 2-ethylhexanol, nonanol, 3,5,5-trimethylhexanol, isononanol, decanol, isodecanol, lauryl alcohol, myristyl alcohol, cetyl alcohol, stearyl alcohol, eicosanol, docosanol, tetracosanol, hexacosanol, octacosanol, nonacosanol, melissyl alcohol and the like.

Examples of polyvalent alcohols include ethylene glycol, propylene glycol, polyalkylene glycols, 1,3-propanediol, 1,4-butanediol, 1,5-pentanediol, 1,6-hexanediol, diethylene glycol, dipropylene glycol, 2,2,4-trimethyl-1,3-pentanediol, spiroglycol, 1,4-phenylene glycol, 1,2,4-butanetriol, 1,2,5-pentanetriol, 1,2,3,6-hexanetetrol, 2-methyl-1,2,4-butanetriol, erythrite, arabitol, sorbitol, mannitol, sorbitan, glycerin, 2-methylpropanetriol, neopentylglycol, 2,2-diethyl-1,3-propane diol, 2-n-butyl-2-ethyl-1,3-propanediol, trimethylolethane, triethylolethane, trimethylolpropane, pentaerythritol, dipentaerythritol, tripentaerythritol, 1,3,5-trihydroxymethylbenzene and the like. Examples of the alkylene oxides that are used for preparing the ether compounds (i.e., alkylene oxide adducts of alcohols as described above) include ethylene oxide, propylene oxide, butylene oxide, and the like.

Examples of hydrocarbon solvents used in the present invention include aromatic hydrocarbon solvents and aliphatic hydrocarbon solvents. Examples of aromatic hydrocarbon solvents include benzene, toluene, and xylene. Examples of aliphatic hydrocarbon solvents include isooctane, n-decane, isodecane, n-undecane, cyclopentane, n-tetradecane, n-tridecane, n-hexadecane, n-hexane, and n-pentane. Among these, toluene, xylene, cyclohexane and normal heptane, which have a boiling point of ordinary level, are particularly preferable. This is because solvents having a relatively low boiling point need special safety measures when being handled, and solvents having a high boiling point need high temperature and a long time to be removed from ester.

As an alcohol solvent used to separate an ester from a crude esterified product obtained by a reaction of a raw material alcohol and a carboxylic acid, alcohols having 1 to 3 carbon atoms are preferable. Examples of such alcohols include methanol, ethanol, normal propanol, and isopropanol. The alcohol solvent for separation is preferably used when neutralizing a crude esterified product that tends to be emulsified or that causes a poor layer separation at the time of a neutralization treatment, for example, a crude esterified product containing a high melting point ester derived from a linear saturated monocarboxylic acid having at least 14 carbon atoms.

Examples of an alkali contained in an alkaline aqueous solution used for the neutralization treatment include alkali metal hydroxides such as sodium hydroxide and potassium hydroxide; alkali metal salts such as sodium carbonate, potassium carbonate, and sodium hydrogencarbonate; an ammonium salts such as ammonium carbonate. Among these, alkali metal hydroxide an alkali metal salts are preferably used.

In the method of the present invention, first, an esterification reaction is performed by a reaction between a carboxylic acid and a raw material alcohol as described above. In this reaction, the kinds and the equivalent ratio of the carboxylic acid and the raw material alcohol are selected as appropriate, depending on the characteristics of a desired ester. The reaction is performed in the presence or absence of a catalyst and generally at a temperature of 120° C. to 240° C. A crude esterified product can be obtained by esterification reaction in above-mentioned manner.

A hydrocarbon solvent as described above is added to the obtained crude esterified product. The hydrocarbon solvent is added in 5 to 100 parts by weight, preferably 5 to 80 parts by weight, more preferably 10 to 60 parts by weight, with respect to 100 parts by weight of the crude esterified product. When the hydrocarbon solvent is added in a ratio of less than 5 parts by weight, a mixture of a crude esterified product and an alkaline aqueous solution tends to be poorly separated into an ester layer and an alkaline aqueous layer, or the mixture is emulsified and cannot be separated. When the hydrocarbon solvent is added in a ratio of more than 100 parts by weight, the effect of separating the layers or preventing emulsification cannot be obtained in proportion to the added amount, and furthermore a process for removing the solvent requires a long time and thus the productivity is reduced.

When treating a crude esterified product that tends to be emulsified or that causes poor layer separation in the process of neutralization, it is preferable to add an alcohol for separation, as described above. The addition of an alcohol for separation further improves the layer separation during a neutralization treatment, and thus improves the yield of esters. The amount of the alcohol solvent added is 50 parts by weight or less, preferably 3 to 50 parts by weight, more preferably 5 to 30 parts by weight, with respect to 100 parts by weight of the crude esterified product.

The concentration of the alkali contained in an alkaline aqueous solution used for the neutralization treatment is preferably 5 to 20 wt %, and an amount of the alkali contained in the aqueous solution is a 1 to 2 equivalents with respect to the acid value of the crude esterified product.

The neutralization treatment is performed by mixing the crude esterified product, the hydrocarbon solvent, the alkaline aqueous solution and, if necessary, the alcohol solvent in order to neutralize acids present in the crude esterified product with alkali. In general, the hydrocarbon solvent and, if necessary, the alcohol solvent are added to the crude esterified product, and then the alkaline aqueous solution is added thereto and the resultant mixture is sufficiently stirred with heating. The temperature at which the neutralization treatment is performed can be selected as appropriate, depending on the viscosity of the crude esterified product, but generally it is 50 to 100° C., preferably 70 to 90° C. A temperature of less than 50° C. may cause poor layer separation or emulsification, and a temperature of more than 100° C. may cause ester to be hydrolyzed.

An oil layer (i.e., an ester layer) containing an ester and an alkaline aqueous layer are separated by the neutralization treatment, and the alkaline aqueous layer is removed. Next, the ester layer is washed with water using 5 to 100 parts by weight of warm water or hot water (50 to 100° C.) with respect to 100 parts by weight of the crude esterified product. The washing with water is repeated until the waste water after washing becomes substantially neutral (e.g., pH of 7 or less which is around pH 7). Then, the solvent contained in the ester layer is removed by distillation under reduced pressure, and thus a desired ester can be obtained.

The quality of the obtained ester can be further improved by a purification treatment employing adsorption or distillation. Purification treatment employing adsorption refers to a treatment in which an adsorbent and the obtained ester are mixed and filtrated, and thus, recovering a purified ester. As the adsorbent, for example, activated clay, acid clay, a silica-alumina synthetic adsorbent, synthetic zeolite, activated carbon and silica gel can be used. Among the above-listed adsorbents, activated clay and acid clay can be used preferably to reduce a coloring substance, resins and unsaturated compounds in the ester. Synthetic zeolite can be used preferably to reduce metal ions. Activated carbon or synthetic adsorbents can be used preferably to reduce the oxidation of the ester and to improve the stability. These adsorbents can be used alone or in combination in view of the quality, the function, the purity or the like required for the ester.

Purification by distillation is performed in order to improve the purity of the ester. There is no particular limitation regarding the distillation method, but molecular distillation is preferable. As an apparatus for molecular distillation, for example, a Smith type distillatory is used preferably.

As described above, in the method for producing an ester of the present invention, a predetermined amount of the hydrocarbon solvent is used, so that poor layer separation or emulsification does not occur during the neutralization treatment, and thus a high-quality ester can be obtained with high yield.

The production method of the present invention can be employed for production of various types of esters. The present invention can be employed preferably to produce, for example, a wax ester with high melting point (e.g., 50 to 100° C.) derived from a long chain carboxylic acid and having a small content of a low volatile substance or a high viscosity ester (e.g., ester having a kinematic viscosity of 60 to 50,000 mm$^2$/s at 40° C.) that is liquid at room temperature and that has excellent heat stability and high insulation properties.

The wax ester having a high melting point obtained by the present invention has small content of low volatile substances, raw material alcohols, raw material carboxylic acids and esters having a hydroxyl group, and thus, exhibits sharp melting characteristics. Therefore, this ester can be effectively used for a releasing agent for toner.

The high viscosity ester that is liquid at room temperature obtained by the present invention has excellent heat stability and electric insulation properties. Therefore, this ester is useful for applications that require high levels of heat stability and electric insulation properties, for example, lublicants for refrigerating machine oil and special grease.

EXAMPLES

The present invention will be described more specifically by illustrating methods for producing esters by way of the following examples. However, the present invention is not limited to these examples.

Example 1

First, 230.0 g (1.69 mol) of pentaerythritol and 1975.9 g (6.96 mol) of stearic acid were put in a 3 liter four-necked flask provided with a thermometer, a nitrogen inlet tube, a stirrer and a condenser, and a reaction was conducted at atmospheric pressure under a nitrogen stream at 220° C. for 15 hours while removing water that was produced by the reaction by distillation. Thus, a crude esterified product was obtained in an amount of 2042.6 g, and the acid value thereof was 10.5 mgKOH/g.

Then, 200 g of toluene and 260 g of isopropanol were added to 1000.0 g of the crude esterified product (i.e., 20 parts by weight of a hydrocarbon solvent and 26 parts by weight of an alcohol solvent were added with respect to 100 parts by weight of the crude esterified product). Then, a 10% potassium hydroxide aqueous solution containing an amount of potassium hydroxide that corresponds to 1.5 equivalents of the acid value of this crude esterified product was added thereto, and the mixture was stirred at 70° C. for 30 minutes. This mixture was allowed to stand for 30 minutes and the aqueous layer was removed, and thus a neutralization process was completed. Then, ion exchanged water was added in an amount of 20 parts by weight with respect to 100 parts by weight of the crude esterified product, and the mixture was stirred at 70° C. for 30 minutes and then allowed to stand for 30 minutes, followed by removal of the aqueous layer. This water washing process was repeated four times until the pH of the waste water became neutral. Then, the solvent in the ester layer was removed by distillation under a reduced pressure of 1 kPa at 180° C., and the resultant mixture was filtrated. Thus, an ester having a melting point of 77.3° C., an acid value of 0.07 mgKOH/g, a hydroxyl value of 0.8 mgKOH/g, and a color number (APHA) of 50 was obtained in an amount of 952.3 g, as a final product. The yield of the ester with respect to the crude esterified product that was subjected to the neutralization treatment was 95.2%.

Table 1 shows the conditions for the neutralization treatment of Example 1, the state of the separation, and the yield and the properties of the obtained ester. Tables 1 to 3 show the experimental data of Examples 2 to 14 and Comparative Examples 1 to 14 described below.

Comparative Example 1

First, 20 g of toluene were added to 1000.0 g of the crude esterified product of Example 1 (i.e., 2 parts by weight of a hydrocarbon solvent was added with respect to 100 parts by weight of the crude esterified product). Then, a 10% potassium hydroxide aqueous solution containing an amount of potassium hydroxide that corresponds to 1.5 equivalents of the acid value of this crude esterified product was added thereto, and the mixture was stirred at 90° C. for 30 minutes. Although the mixture was allowed to stand for 30 minutes, the mixture was not separated into an ester layer and an alkali aqueous layer, and the entire mixture was in an emulsion state, and thus, the aqueous layer could not be removed. Then, 100 g of 10% sodium sulfate hot water solution were added, and the mixture was stirred at 90° C. for 30 minutes and then allowed to stand for 30 minutes, followed by removal of the aqueous layer. This water washing process was repeated four times until the pH of the waste water became neutral. Then, the solvent in the ester layer was removed by distillation under a reduced pressure of 1 kPa at 180° C., and the resultant mixture was filtrated. Thus, an ester having a melting point of 75.1° C., an acid value of 0.35 mgKOH/g, a hydroxyl value of 0.8 mgKOH/g, and a color number (APHA) of 90 was obtained in an amount of 903.2 g, as a final product. The yield of the ester with respect to the crude esterified product that was subjected to the neutralization treatment was 90.3%.

Example 2

First, 240.0 g (1.76 mol) of pentaerythritol, 743.4 g (2.90 mol) of palmitic acid, and 1237.1 g (4.36 mol) of stearic acid were put in a 3 liter four-necked flask provided with a thermometer, a nitrogen inlet tube, a stirrer and a condenser, and a reaction was conducted at atmospheric pressure under a nitrogen stream at 220° C. for 15 hours while removing water that was produced by the reaction by distillation. Thus, a crude esterified product was obtained in an amount of 2051.8 g, and the acid value thereof was 10.5 mgKOH/g.

Then, 80 g of toluene and 100 g of isopropanol were added to 1000.0 g of the crude esterified product (i.e., 8 parts by weight of a hydrocarbon solvent and 10 parts by weight of an alcohol solvent were added with respect to 100 parts by weight of the crude esterified product). Then, a 10% potassium hydroxide aqueous solution containing an amount of potassium hydroxide that corresponds to 1.5 equivalents of the acid value of this crude esterified product was added thereto, and the mixture was stirred at 70° C. for 30 minutes. This mixture was allowed to stand for 30 minutes and the aqueous layer was removed, and thus a neutralization process was completed. Then, ion exchanged water was added in an amount of 20 parts by weight with respect to 100 parts by weight of the crude esterified product, and the mixture was stirred at 70° C. for 30 minutes and then allowed to stand for 30 minutes, followed by removal of the aqueous layer. This water washing process was repeated five times until the pH of the waste water became neutral. Then, the solvent in the ester layer was removed by distillation under a reduced pressure of 1 kPa at 180° C. Then, an adsorption process was performed by adding 5 g of activated clay SA-1 (manufactured by Nihon Kassei Hakudo) and 5 g of activated alumina DN-1A (manufactured by Mizusawa Chemical Industries). The temperature, the pressure and the time during the adsorption process were 100° C., 1 kPa and three hours, respectively. Then, the resultant mixture was filtrated. Thus, an ester having a melting point of 67.7° C., an acid value of 0.2 mgKOH/g, a hydroxyl value of 1.5 mgKOH/g, and a color number (APHA) of 60 was obtained in an amount of 941.2 g, as a final product. The yield of the ester with respect to the crude esterified product that was subjected to the neutralization treatment was 94.1%.

Comparative Example 2

First, 100 g of isopropanol were added to 1000.0 g of the crude esterified product of Example 2 (i.e., 10 parts by weight of an alcohol solvent was added with respect to 100 parts by weight of the crude esterified product). Then, a 10% potassium hydroxide aqueous solution containing an amount of potassium hydroxide that corresponds to 1.5 equivalents of the acid value of this crude esterified product was added thereto, and the mixture was stirred at 70° C. for 30 minutes. Although the mixture was allowed to stand for 30 minutes, the mixture was not separated into an ester layer and an alkali aqueous layer, and the entire mixture was in an emulsion state, and the aqueous layer could not be removed. Thereafter, the ester layer was dehydrated under a reduced pressure of 1 kPa at 100° C. Then, an adsorption process was performed by adding 5 g of activated clay SA-1 (manufactured by Nihon Kassei Hakudo) and 5 g of activated alumina DN-1A (manufactured by Mizusawa Chemical Industries). The temperature, the pressure and the time during the adsorption process were 100° C., 1 kPa and three hours, respectively. Then, the resultant mixture was filtrated. Thus, an ester having a melting point of 63.4° C., an acid value of 0.7 mgKOH/g, a hydroxyl value of 1.5 mgKOH/g, and a color number (APHA) of 90 was obtained in an amount of 94.6 g, as a final product. The yield of the ester with respect to the crude esterified product that was subjected to the neutralization treatment was 94.6%.

Example 3

First, 400.0 g (2.98 mol) of trimethylolpropane and 1842.0 g (9.21 mol) of lauric acid were put in a 3 liter four-necked flask provided with a thermometer, a nitrogen inlet tube, a stirrer and a condenser, and a reaction was conducted at atmospheric pressure under a nitrogen stream at 220° C. for 15 hours while removing water that was produced by the reaction by distillation. Thus, a crude esterified product was obtained in an amount of 2039.4 g, and the acid value thereof was 8.8 mgKOH/g.

Then, 50 g of normal heptane and 100 g of ethanol were added to 1000.0 g of the crude esterified product (i.e., 5 parts by weight of a hydrocarbon solvent and 10 parts by weight of an alcohol solvent were added with respect to 100 parts by weight of the crude esterified product). Then, a 10% potassium hydroxide aqueous solution containing an amount of potassium hydroxide that corresponds to 1.5 equivalents of the acid value of this crude esterified product was added thereto, and the mixture was stirred at 70° C. for 30 minutes. This mixture was allowed to stand for 30 minutes and the aqueous layer was removed, and thus a neutralization process was completed. Then, ion exchanged water was added in an amount of 20 parts by weight with respect to 100 parts by weight of the crude esterified product, and the mixture was stirred at 70° C. for 30 minutes and then allowed to stand for 30 minutes, followed by removal of the aqueous layer. This water washing process was repeated five times until the pH of the waste water became neutral. Then, the solvent in the ester layer was removed by distillation under a reduced pressure of 1 kPa at 180° C. Then, an adsorption process was performed by adding 5 g of activated clay SA-1 (manufactured by Nihon Kassei Hakudo) and 5 g of activated alumina DN-1A (manufactured by Mizusawa Chemical Industries). The temperature, the pressure and the time during the adsorption process were 100° C., 1 kPa and three hours, respectively. Then, the resultant mixture was filtrated. Thus, an ester having a melting point of 28.0° C., an acid value of 0.2 mgKOH/g, a hydroxyl value of 1.4 mgKOH/g, and a color number (APHA) of 50 was obtained in an amount of 902.1 g, as a final product. The yield of the ester with respect to the crude esterified product that was subjected to the neutralization treatment was 90.2%.

Comparative Example 3

First, 100 g of methanol were added to 1000.0 g of the crude esterified product of Example 3 (i.e., 10 parts by weight of an alcohol solvent was added with respect to 100 parts by weight of the crude esterified product). Then, a 10% potassium hydroxide aqueous solution containing an amount of potassium hydroxide that corresponds to 1.5 equivalents of the acid value of this crude esterified product was added thereto, and the mixture was stirred at 60° C. for 30 minutes. When the mixture was allowed to stand for 30 minutes, an emulsified layer was formed between an ester layer and an alkali aqueous layer, and the aqueous layer was removed. Then, the resultant mixture was washed with water five times until the pH of the waste water became neutral. Thereafter, the ester layer was dehydrated under a reduced pressure of 1 kPa at 100° C. Then, an adsorption process was performed by adding 5 g of activated clay SA-1 (manufactured by Nihon Kassei Hakudo) and 5 g of activated alumina DN-1A (manufactured by Mizusawa Chemical Industries). The temperature, the pressure and the time during the adsorption process were 100° C., 1 kPa and three hours, respectively. Then, the resultant mixture was filtrated. Thus, an ester having a melting point of 24.5° C., an acid value of 0.4 mgKOH/g, a hydroxyl value of 1.4 mgKOH/g, and a color number (APHA) of 90 was obtained in an amount of 843.1 g, as a final product. The yield of the ester with respect to the crude esterified product that was subjected to the neutralization treatment was 84.3%.

Example 4

First, 340.0 g (2.53 mol) of trimethylolpropane and 2004.0 g (7.83 mol) of palmitic acid were put in a 3 liter four-necked flask provided with a thermometer, a nitrogen inlet tube, a stirrer and a condenser, and a reaction was conducted at atmospheric pressure under a nitrogen stream at 220° C. for 15 hours while removing water that was produced by the reaction by distillation. Thus, a crude esterified product was obtained in an amount of 2163.1 g, and the acid value thereof was 9.2 mgKOH/g.

Then, 150 g of cyclohexane and 100 g of ethanol were added to 1000.0 g of the crude esterified product (i.e., 15 parts by weight of a hydrocarbon solvent and 10 parts by weight of an alcohol solvent were added with respect to 100 parts by weight of the crude esterified product). Then, a 10% potassium hydroxide aqueous solution containing an amount of potassium hydroxide that corresponds to 1.5 equivalents of the acid value of this crude esterified product was added thereto, and the mixture was stirred at 70° C. for 30 minutes. This mixture was allowed to stand for 30 minutes and the aqueous layer was removed, and thus a neutralization process was completed. Then, ion exchanged water was added in an amount of 20 parts by weight with respect to 100 parts by weight of the crude esterified product, and the mixture was stirred at 70° C. for 30 minutes and then allowed to stand for 30 minutes, followed by removal of the aqueous layer. This water washing process was repeated five times until the pH of the waste water became neutral. Then, the solvent in the ester layer was removed by distillation under a reduced pressure of 1 kPa at 180° C. Then, an adsorption process was performed by adding 5 g of Kyowaad 500SH (manufactured by Kyowa Chemical Industry Co., Ltd). The temperature, the pressure and the time during the adsorption process were 100° C., 1 kPa and three hours, respectively. Then, the resultant mixture was filtrated. Thus, an ester having a melting point of 45.5° C., an acid value of 0.4 mgKOH/g, a hydroxyl value of 2.2 mgKOH/g, and a color number (APHA) of 60 was obtained in an amount of 951.2 g, as a final product. The yield of the ester with respect to the crude esterified product that was subjected to the neutralization treatment was 95.1%.

Comparative Example 4

First, 15 g of cyclohexane were added to 1000.0 g of the crude esterified product of Example 4 (i.e., 1.5 parts by weight of a hydrocarbon solvent was added with respect to 100 parts by weight of the crude esterified product). Then, a 10% potassium hydroxide aqueous solution containing an amount of potassium hydroxide that corresponds to 1.5 equivalents of the acid value of this crude esterified product was added thereto, and the mixture was stirred at 70° C. for 30 minutes. Although the mixture was allowed to stand for 30 minutes, the mixture was not separated into an ester layer and an alkali aqueous layer, and the entire mixture was in an emulsion state, and the aqueous layer could not be removed.

Then, 100 g of 10% sodium sulfate hot water solution were added, and the mixture was stirred at 70° C. for 30 minutes and then allowed to stand for 30 minutes, followed by removal of the aqueous layer. The resultant mixture was washed with water five times until the pH of the waste water became neutral. Then, the solvent in the ester layer was removed by distillation under a reduced pressure of 1 kPa at 180° C. Then, an adsorption process was performed by adding 5 g of Kyowaad 500SH (manufactured by Kyowa Chemical Industry Co., Ltd). The temperature, the pressure and the time during the adsorption process were 100° C., 1 kPa and three hours, respectively. Then, the resultant mixture was filtrated. Thus, an ester having a melting point of 42.5° C., an acid value of 1.2 mgKOH/g, a hydroxyl value of 2.2 mgKOH/g, and a color number (APHA) of 80 was obtained in an amount of 913.3 g, as a final product. The yield of the ester with respect to the crude esterified product that was subjected to the neutralization treatment was 91.3%.

Example 5

First, 160.0 g (2.08 mol) of trimethylolmethane and 2000.0 g (6.41 mol) of arachic acid were put in a 3 liter four-necked flask provided with a thermometer, a nitrogen inlet tube, a stirrer and a condenser, and a reaction was conducted at atmospheric pressure under a nitrogen stream at 220° C. for 15 hours while removing water that was produced by the reaction by distillation. Thus, a crude esterified product was obtained in an amount of 2006.8 g, and the acid value thereof was 9.0 mgKOH/g.

Then, 100 g of xylene and 100 g of isopropanol were added to 1000.0 g of the crude esterified product (i.e., 10 parts by weight of a hydrocarbon solvent and 10 parts by weight of an alcohol solvent were added with respect to 100 parts by weight of the crude esterified product). Then, a 10% potassium hydroxide aqueous solution containing an amount of potassium hydroxide that corresponds to 1.5 equivalents of the acid value of this crude esterified product was added thereto, and the mixture was stirred at 70° C. for 30 minutes. This mixture was allowed to stand for 30 minutes and the aqueous layer was removed, and thus a neutralization process was completed. Then, ion exchanged water was added in an amount of 20 parts by weight with respect to 100 parts by weight of the crude esterified product, and the mixture was stirred at 70° C. for 30 minutes and then allowed to stand for 30 minutes, followed by removal of the aqueous layer. This water washing process was repeated five times until the pH of the waste water became neutral. Then, the solvent in the ester layer was removed by distillation under a reduced pressure of 1 kPa at 180° C. Then, an adsorption process was performed by adding 5 g of Kyowaad 500SH (manufactured by Kyowa Chemical Industry Co., Ltd). The temperature, the pressure and the time during the adsorption process were 100° C., 1 kPa and three hours, respectively. Then, the resultant mixture was filtrated. Thus, an ester having a melting point of 74.0° C., an acid value of 0.2 mgKOH/g, a hydroxyl value of 3.3 mgKOH/g, and a color number (APHA) of 40 was obtained in an amount of 948.2 g, as a final product. The yield of the ester with respect to the crude esterified product that was subjected to the neutralization treatment was 94.8%.

Comparative Example 5

An adsorption process was performed by adding 5 g of Kyowaad 500SH (manufactured by Kyowa Chemical Industry Co., Ltd) to 1000.0 g of the crude esterified product of Example 5. The temperature, the pressure and the time during the adsorption process were 100° C., 1 kPa and three hours, respectively. Then, the resultant mixture was filtrated. Thus, an ester having a melting point of 68.2° C., an acid value of 8.9 mgKOH/g, a hydroxyl value of 3.3 mgKOH/g, and a color number (APHA) of 140 was obtained in an amount of 965.2 g, as a final product. The yield of the ester with respect to the crude esterified product that was subjected to the neutralization treatment was 96.5%.

Example 6

First, 300.0 g (3.26 mol) of glycerin and 2013.0 g (10.07 mol) of lauric acid were put in a 3 liter four-necked flask provided with a thermometer, a nitrogen inlet tube, a stirrer and a condenser, and a reaction was conducted at atmospheric pressure under a nitrogen stream at 220° C. for 15 hours while removing water that was produced by the reaction by distillation. Thus, a crude esterified product was obtained in an amount of 2115.7 g, and the acid value thereof was 6.9 mgKOH/g.

Then, 50 g of cyclohexane and 100 g of isopropanol were added to 1000.0 g of the crude esterified product (i.e., 5 parts by weight of a hydrocarbon solvent and 10 parts by weight of an alcohol solvent were added with respect to 100 parts by weight of the crude esterified product). Then, a 10% potassium hydroxide aqueous solution containing an amount of potassium hydroxide that corresponds to 1.5 equivalents of the acid value of this crude esterified product was added thereto, and the mixture was stirred at 70° C. for 30 minutes. The resultant mixture was allowed to stand for 30 minutes and the aqueous layer was removed, and thus a neutralization process was completed. Then, ion exchanged water was added in an amount of 20 parts by weight with respect to 100 parts by weight of the crude esterified product, and the mixture was stirred at 70° C. for 30 minutes and then allowed to stand for 30 minutes, followed by removal of the aqueous layer. This water washing process was repeated five times until the pH of the waste water became neutral. Then, the solvent in the ester layer was removed by distillation under a reduced pressure of 1 kPa at 180° C. Then, an adsorption process was performed by adding 5 g of activated clay SA-1 (manufactured by Nihon Kassei Hakudo) and 5 g of activated alumina DN-1A (manufactured by Mizusawa Chemical Industries). The temperature, the pressure and the time during the adsorption process were 100° C., 1 kPa and three hours, respectively. Then, the resultant mixture was filtrated. Thus, an ester having a melting point of 46.4° C., an acid value of 0.2 mgKOH/g, a hydroxyl value of 1.5 mgKOH/g, and a color number (APHA) of 40 was obtained in an amount of 925.3 g, as a final product. The yield of the ester with respect to the crude esterified product that was subjected to the neutralization treatment was 92.5%.

Comparative Example 6

To 1000.0 g of the crude esterified product of Example 6, a 10% potassium hydroxide aqueous solution containing an amount of potassium hydroxide that corresponds to 1.5 equivalents of the acid value of this crude esterified product was added. Then, the resultant mixture was stirred at 70° C. for 30 minutes. Although the mixture was allowed to stand for 30 minutes, the mixture was not separated into an ester layer and an alkali aqueous layer, and the entire mixture was in an emulsion state, and the aqueous layer could not be removed. Then, 100 g of 10% sodium sulfate hot water solution were added, and the mixture was stirred at 70° C. for 30 minutes and then allowed to stand for 30 minutes, followed by removal of the aqueous layer. The resultant mixture was washed with water five times until the pH of the waste water became neutral. Then, the solvent in the ester layer was removed by distillation under a reduced pressure of 1 kPa at 180° C.

Then, an adsorption process was performed by adding 5 g of activated clay SA-1 (manufactured by Nihon Kassei Hakudo) and 5 g of activated alumina DN-1A (manufactured by Mizusawa Chemical Industries). The temperature, the pressure and the time during the adsorption process were 100° C., 1 kPa and three hours, respectively. Then, the resultant mixture was filtrated. Thus, an ester having a melting point of 42.1° C., an acid value of 0.7 mgKOH/g, a hydroxyl value of 1.5 mgKOH/g, and a color number (APHA) of 80 was obtained in an amount of 861.2 g, as a final product. The yield of the ester with respect to the crude esterified product that was subjected to the neutralization treatment was 86.1%.

Example 7

First, 300.0 g (1.18 mol) of dipentaerythritol, 1993.2 g (7.79 mol) of palmitic acid and 2.3 g of p-toluenesulfonic acid were put in a 3 liter four-necked flask provided with a thermometer, a nitrogen inlet tube, a stirrer and a condenser, and a reaction was conducted at atmospheric pressure under a nitrogen stream at 220° C. for 15 hours while removing water that was produced by the reaction by distillation. Thus, a crude esterified product was obtained in an amount of 2144.2 g, and the acid value thereof was 21.1 mgKOH/g.

Then, 230 g of cyclohexane and 120 g of ethanol were added to 1000.0 g of the crude esterified product (i.e., 23 parts by weight of a hydrocarbon solvent and 12 parts by weight of an alcohol solvent were added with respect to 100 parts by weight of the crude esterified product). Then, a 10% potassium hydroxide aqueous solution containing an amount of potassium hydroxide that corresponds to 1.5 equivalents of the acid value of this crude esterified product was added thereto, and the mixture was stirred at 75° C. for 30 minutes. This mixture was allowed to stand for 30 minutes and the aqueous layer was removed, and thus a neutralization process was completed. Then, ion exchanged water was added in an amount of 20 parts by weight with respect to 100 parts by weight of the crude esterified product, and the mixture was stirred at 75° C. for 30 minutes and then allowed to stand for 30 minutes, followed by removal of the aqueous layer. This water washing process was repeated four times until the pH of the waste water became neutral. Then, the solvent in the ester layer was removed by distillation under a reduced pressure of 1 kPa at 180° C., and the resultant mixture was filtrated. Thus, an ester having a melting point of 73.2° C., an acid value of 0.09 mgKOH/g, a hydroxyl value of 1.2 mgKOH/g, and a color number (APHA) of 60 was obtained in an amount of 889.4 g, as a final product. The yield of the ester with respect to the crude esterified product that was subjected to the neutralization treatment was 88.9%.

Comparative Example 7

To 1000.0 g of the crude esterified product of Example 7, a 10% potassium hydroxide aqueous solution containing an amount of potassium hydroxide that corresponds to 1.5 equivalents of the acid value of this crude esterified product was added. Then, the resultant mixture was stirred at 90° C. for 30 minutes. Although the mixture was allowed to stand for 30 minutes, the mixture was not separated into an ester layer and an alkali aqueous layer, and the entire mixture was in an emulsion state, and the aqueous layer could not be removed. Then, 250 g of 20% sodium sulfate hot water solution were added, and the mixture was stirred at 90° C. for 30 minutes and then allowed to stand for 30 minutes, followed by removal of the aqueous layer. The resultant mixture was washed with water four times until the pH of the waste water became neutral. Then, the ester layer was dehydrated under a reduced pressure of 1 kPa at 900C., and the resultant mixture was filtered. Thus, an ester having a melting point of 71.8° C., an acid value of 0.60 mgKOH/g, a hydroxyl value of 1.2 mgKOH/g, and a color number (APHA) of 100 was obtained in an amount of 843.3 g, as a final product. The yield of the ester with respect to the crude esterified product that was subjected to the neutralization treatment was 84.3%.

Example 8

First, 1050.0 g (3.22 mol) of behenyl alcohol, 1127.9 g (3.32 mol) of behenic acid and 2.2 g of p-toluenesulfonic acid were put in a 3 liter four-necked flask provided with a thermometer, a nitrogen inlet tube, a stirrer and a condenser, and a reaction was conducted at atmospheric pressure under a nitrogen stream at 220° C. for 15 hours while removing water that was produced by the reaction by distillation. Thus, a crude esterified product was obtained in an amount of 2107.2 g, and the acid value thereof was 8.9 mgKOH/g. Then, 130 g of toluene, 60 g of xylene, 30 g of isopropanol and 240 g of ethanol were added to 1000.0 g of the crude esterified product (i.e., 19 parts by weight of a hydrocarbon solvent and 27 parts by weight of an alcohol solvent were added with respect to 100 parts by weight of the crude esterified product). Then, a 10% potassium hydroxide aqueous solution containing an amount of potassium hydroxide that corresponds to 1.5 equivalents of the acid value of this crude esterified product was added thereto, and the mixture was stirred at 75° C. for 30 minutes. This mixture was allowed to stand for 30 minutes and the aqueous layer was removed, and thus a neutralization process was completed. Then, ion exchanged water was added in an amount of 20 parts by weight with respect to 100 parts by weight of the crude esterified product, and the mixture was stirred at 70° C. for 30 minutes and then allowed to stand for 30 minutes, followed by removal of the aqueous layer. This water washing process was repeated four times until the pH of the waste water became neutral. Then, the solvent in the ester layer was removed by distillation under a reduced pressure of 1.0 kPa at 180° C., and the resultant mixture was filtered. Thus, an ester having a melting point of 73.0° C., an acid value of 0.08 mgKOH/g, a hydroxyl value of 0.9 mgKOH/g, and a color number (APHA) of 55 was obtained in an amount of 954.4 g, as a final product. The yield of the ester with respect to the crude esterified product that was subjected to the neutralization treatment was 95.4%.

Comparative Example 8

An adsorption process was performed by adding 10 g of Galleon Earth V2 (manufactured by Mizusawa Chemical Industries) and 10 g of Tomita AD300P (manufactured by Tomita Pharmaceutical Co. Ltd.) to 1000.0 g of the crude esterified product of Example 8. The temperature, the pressure and the time during the adsorption process were 100° C., 1 kPa and three hours, respectively. Then, the resultant mixture was filtered. Thus, an ester having a melting point of 70.1° C., an acid value of 8.4 mgKOH/g, a hydroxyl value of 0.9 mgKOH/g, and a color number (APHA) of 90 was obtained in an amount of 973.6 g, as a final product. The yield of the ester with respect to the crude esterified product that was subjected to the adsorption process was 97.4%.

Example 9

First, 1800.0 g (6.69 mol) of stearyl alcohol and 482.8 g (2.30 mol) of trimellitic acid were put in a 3 liter four-necked flask provided with a thermometer, a nitrogen inlet tube, a stirrer and a condenser, and a reaction was conducted at atmospheric pressure under a nitrogen stream at 220° C. for 15 hours while removing water that was produced by the reaction by distillation. Thus, a crude esterified product was obtained in an amount of 2140.7 g, and the acid value thereof was 10.1 mgKOH/g.

Then, 100 g of toluene and 120 g of ethanol were added to 1000.0 g of the crude esterified product (i.e., 10 parts by weight of a hydrocarbon solvent and 12 parts by weight of an alcohol solvent were added with respect to 100 parts by weight of the crude esterified product). Then, a 10% potassium hydroxide aqueous solution containing an amount of potassium hydroxide that corresponds to 1.5 equivalents of the acid value of this crude esterified product was added thereto, and the mixture was stirred at 70° C. for 30 minutes. This mixture was allowed to stand for 30 minutes and the aqueous layer was removed, and thus a neutralization process was completed. Then, ion exchanged water was added in an amount of 20 parts by weight with respect to 100 parts by weight of the crude esterified product, and the mixture was stirred at 70° C. for 30 minutes and then allowed to stand for 30 minutes, followed by removal of the aqueous layer. This water washing process was repeated five times until the pH of the waste water became neutral. Then, the solvent in the ester layer was removed by distillation under a reduced pressure of 1 kPa at 180° C. Then, an adsorption process was performed by adding 5 g of activated clay SA-1 (manufactured by Nihon Kassei Hakudo) and 5 g of activated alumina DN-1A (manufactured by Mizusawa Chemical Industries). The temperature, the pressure and the time during the adsorption process were 100° C., 1 kPa and three hours, respectively. Then, the resultant mixture was filtered. Thus, an ester having a melting point of 68.2° C., an acid value of 0.3 mgKOH/g, a hydroxyl value of 2.7 mgKOH/g, and a color number (APHA) of 55 was obtained in an amount of 943.2 g, as a final product. The yield of the ester with respect to the crude esterified product that was subjected to the neutralization treatment was 94.3%.

Comparative Example 9

An adsorption process was performed by adding 5 g of activated clay SA-1 (manufactured by Nihon Kassei Hakudo) and 5 g of activated alumina DN-1A (manufactured by Mizusawa Chemical Industries) to 1000.0 g of the crude esterified product of Example 9. The temperature, the pressure and the time during the adsorption process were 100° C., 1 kPa and three hours, respectively. Then, the resultant mixture was filtered. Thus, an ester having a melting point of 65.4° C., an acid value of 9.9 mgKOH/g, a hydroxyl value of 2.7 mgKOH/g, and a color number (APHA) of 100 was obtained in an amount of 968.3 g, as a final product. The yield of the ester with respect to the crude esterified product that was subjected to the neutralization treatment was 96.8%.

Example 10

First, 1400.0 g (7.57 mol) of lauryl alcohol and 819.0 g (3.90 mol) of terephthalic acid were put in a 3 liter four-necked flask provided with a thermometer, a nitrogen inlet tube, a stirrer and a condenser, and a reaction was conducted at atmospheric pressure under a nitrogen stream at 220° C. for 15 hours while removing water that was produced by the reaction by distillation. Thus, a crude esterified product was obtained in an amount of 2062.0 g, and the acid value thereof was 9.9 mgKOH/g.

Then, 150 g of toluene and 100 g of isopropanol were added to 1000.0 g of the crude esterified product (i.e., 15 parts by weight of a hydrocarbon solvent and 10 parts by weight of an alcohol solvent were added with respect to 100 parts by weight of the crude esterified product). Then, a 10% potassium hydroxide aqueous solution containing an amount of potassium hydroxide that corresponds to 1.5 equivalents of the acid value of this crude esterified product was added thereto, and the mixture was stirred at 80° C. for 30 minutes. This mixture was allowed to stand for 30 minutes and the aqueous layer was removed, and thus a neutralization process was completed. Then, ion exchanged water was added in an amount of 20 parts by weight with respect to 100 parts by weight of the crude esterified product, and the mixture was stirred at 80° C. for 30 minutes and then allowed to stand for 30 minutes, followed by removal of the aqueous layer. This water washing process was repeated five times until the pH of the waste water became neutral. Then, the solvent in the ester layer was removed by distillation under a reduced pressure of 1 kPa at 180° C. Then, an adsorption process was performed by adding 5 g of activated carbon Shirasagi C (manufactured by Takeda Chemical Industries, Ltd.). The temperature, the pressure and the time during the adsorption process were 100° C., 1 kPa and three hours, respectively. Then, the resultant mixture was filtrated. Thus, an ester having a melting point of 68.2° C., an acid value of 0.2 mgKOH/g, a hydroxyl value of 3.2 mgKOH/g, and a color number (APHA) of 70 was obtained in an amount of 936.4 g, as a final product. The yield of the ester with respect to the crude esterified product that was subjected to the neutralization treatment was 93.6%.

Comparative Example 10

First, 20 g of toluene were added to 1000.0 g of the crude esterified product of Example 10 (i.e., 2 parts by weight of a hydrocarbon solvent was added with respect to 100 parts by weight of the crude esterified product). Then, a 10% potassium hydroxide aqueous solution containing an amount of potassium hydroxide that corresponds to 1.5 equivalents of the acid value of this crude esterified product was added thereto, and the mixture was stirred at 80° C. for 30 minutes. Although the mixture was allowed to stand for 30 minutes, the mixture was not separated into an ester layer and an alkali aqueous layer, and the entire mixture was in an emulsion state, and the aqueous layer could not be removed. Thereafter, the ester layer was dehydrated under a reduced pressure of 1 kPa at 80° C. Then, an adsorption process was performed by adding 5 g of activated carbon Shirasagi C (manufactured by Takeda Chemical Industries, Ltd.). The temperature, the pressure and the time during the adsorption process were 100° C., 1 kPa and three hours, respectively. Then, the resultant mixture was filtrated. Thus, an ester having a melting point of 66.4° C., an acid value of 0.8 mgKOH/g, a hydroxyl value of 3.2 mgKOH/g, and a color number (APHA) of 150 was obtained in an amount of 950.2 g, as a final product. The yield of the ester with respect to the crude esterified product that was subjected to the neutralization treatment was 95.0%.

Example 11

First, 1400.0 g (7.57 mol) of lauryl alcohol and 819.0 g (3.90 mol) of terephthalic acid were put in a 3 liter four-necked flask provided with a thermometer, a nitrogen inlet tube, a stirrer and a condenser, and a reaction was conducted at atmospheric pressure under a nitrogen stream at 220° C. for 15 hours while removing water that was produced by the reaction by distillation. Thus, a crude esterified product was obtained in an amount of 2062.0 g, and the acid value thereof was 9.9 mgKOH/g.

Then, 150 g of toluene and 100 g of isopropanol were added to 1000.0 g of the crude esterified product (i.e., 15 parts by weight of a hydrocarbon solvent and 10 parts by weight of an alcohol solvent were added with respect to 100 parts by weight of the crude esterified product). Then, a 10% potassium hydroxide aqueous solution containing an amount of potassium hydroxide that corresponds to 1.5 equivalents of the acid value of this crude esterified product was added thereto, and the mixture was stirred at 80° C. for 30 minutes. This mixture was allowed to stand for 30 minutes and the aqueous layer was removed, and thus a neutralization process was completed. Then, ion exchanged water was added in an amount of 20 parts by weight with respect to 100 parts by weight of the crude esterified product, and the mixture was stirred at 80° C. for 30 minutes and then allowed to stand for 30 minutes, followed by removal of the aqueous layer. This water washing process was repeated five times until the pH of the waste water became neutral. Then, the solvent in the ester layer was removed by distillation under a reduced pressure of 1 kPa at 180° C., and the resultant mixture was filtrated. Thus, an ester having a melting point of 68.1° C., an acid value of 0.4 mgKOH/g, a hydroxyl value of 3.2 mgKOH/g, and a color number (APHA) of 140 was obtained in an amount of 952.3 g, as a final product. The yield of the ester with respect to the crude esterified product that was subjected to the neutralization treatment was 95.2%.

Comparative Example 11

First, 20 g of toluene were added to 1000.0 g of the crude esterified product of Example 11 (i.e., 2 parts by weight of a hydrocarbon solvent was added with respect to 100 parts by weight of the crude esterified product). Then, a 10% potassium hydroxide aqueous solution containing an amount of potassium hydroxide that corresponds to 1.5 equivalents of the acid value of this crude esterified product was added thereto, and the mixture was stirred at 80° C. for 30 minutes. Although the mixture was allowed to stand for 30 minutes, the mixture was not separated into an ester layer and an alkali aqueous layer, and the entire mixture was in an emulsion state, and the aqueous layer could not be removed. Thereafter, the ester layer was dehydrated under a reduced pressure of 1 kPa at 80° C., and was filtrated. Thus, an ester having a melting point of 66.2° C., an acid value of 0.9 mgKOH/g, a hydroxyl value of 3.2 mgKOH/g, and a color number (APHA) of 250 was obtained in an amount of 962.1 g, as a final product. The yield of the ester with respect to the crude esterified product that was subjected to the neutralization treatment was 96.2%.

Example 12

First, 300.0 g (3.33 mol) of 1,4-butanediol and 1947.8 g (6.86 mol) of stearic acid were put in-a 3 liter four-necked flask provided with a thermometer, a nitrogen inlet tube, a stirrer and a condenser, and a reaction was conducted at atmospheric pressure under a nitrogen stream at 220° C. for 15 hours while removing water that was produced by the reaction by distillation. The reaction was stopped when the hydroxyl value reached 5 mgKOH/g or less. Thus, a crude esterified product was obtained in an amount of 2106.7 g, and the acid value thereof was 9.7 mgKOH/g.

Then, 200 g of cyclohexane and 100 g of ethanol were added to 1000.0 g of the crude esterified product (i.e., 20 parts by weight of a hydrocarbon solvent and 10 parts by weight of an alcohol solvent were added with respect to 100 parts by weight of the crude esterified product). Then, a 10% potassium hydroxide aqueous solution containing an amount of potassium hydroxide that corresponds to 1.5 equivalents of the acid value of this crude esterified product was added thereto, and the mixture was stirred at 80° C. for 30 minutes. This mixture was allowed to stand for 30 minutes and the aqueous layer was removed, and thus a neutralization process was completed. Then, ion exchanged water was added in an amount of 20 parts by weight with respect to 100 parts by weight of the crude esterified product, and the mixture was stirred at 80° C. for 30 minutes and then allowed to stand for 30 minutes, followed by removal of the aqueous layer. This water washing process was repeated five times until the pH of the waste water became neutral. Then, the solvent in the ester layer was removed by distillation under a reduced pressure of 1 kPa at 180° C. Then, an adsorption process was performed by adding 5 g of activated carbon Shirasagi C (manufactured by Takeda Chemical Industries, Ltd.). The temperature, the pressure and the time during the adsorption process were 100° C., 1 kPa and three hours, respectively. Then, the resultant mixture was filtrated. Thus, an ester having a melting point of 69.0° C., an acid value of 0.2 mgKOH/g, a hydroxyl value of 3.4 mgKOH/g, and a color number (APHA) of 80 was obtained in an amount of 915.1 g, as a final product. The yield of the ester with respect to the crude esterified product that was subjected to the neutralization treatment was 91.5%.

Comparative Example 12

First, 20 g of cyclohexane were added to 1000.0 g of the crude esterified product of Example 12 (i.e., 2 parts by weight of a hydrocarbon solvent was added with respect to 100 parts by weight of the crude esterified product). Then, a 10% potassium hydroxide aqueous solution containing an amount of potassium hydroxide that corresponds to 1.5 equivalents of the acid value of this crude esterified product was added thereto, and the mixture was stirred at 80° C. for 30 minutes. Although the mixture was allowed to stand for 30 minutes, the mixture was not separated into an ester layer and an alkali aqueous layer, and the entire mixture was in an emulsion state, and the aqueous layer could not be removed. Thereafter, the ester layer was dehydrated under a reduced pressure of 1 kPa at 100° C. Then, an adsorption process was performed by adding 5 g of activated carbon Shirasagi C (manufactured by Takeda Chemical Industries, Ltd.). The temperature, the pressure and the time during the adsorption process were 100° C., 1 kPa and three hours, respectively. Then, the resultant mixture was filtrated. Thus, an ester having a melting point of 65.9° C., an acid value of 0.8 mgKOH/g, a hydroxyl value of 3.4 mgKOH/g, and a color number (APHA) of 150 was obtained in an amount of 950.2 g, as a final product. The yield of the ester with respect to the crude esterified product that was subjected to the neutralization treatment was 95.0%.

Example 13

First, 300.0 g (3.33 mol) of 1,4-butanediol and 1947.8 g (6.86 mol) of stearic acid were put in a 3 liter four-necked flask provided with a thermometer, a nitrogen inlet tube, a stirrer and a condenser, and a reaction was conducted at atmospheric pressure under a nitrogen stream at 220° C. for 15 hours while removing water that was produced by the reaction by distillation. The reaction was stopped when the hydroxyl value reached 5 mgKOH/g or less. Thus, a crude esterified product was obtained in an amount of 2106.7 g, and the acid value thereof was 9.7 mgKOH/g.

Then, 200 g of cyclohexane and 100 g of ethanol were added to 1000.0 g of the crude esterified product (i.e., 20 parts by weight of a hydrocarbon solvent and 10 parts by weight of an alcohol solvent were added with respect to 100 parts by weight of the crude esterified product). Then, a 10% potassium hydroxide aqueous solution containing an amount of potassium hydroxide that corresponds to 1.5 equivalents of the acid value of this crude esterified product was added thereto, and the mixture was stirred at 80° C. for 30 minutes. This mixture was allowed to stand for 30 minutes and the aqueous layer was removed, and thus a neutralization process was completed. Then, ion exchanged water was added in an amount of 20 parts by weight with respect to 100 parts by weight of the crude esterified product, and the mixture was stirred at 80° C. for 30 minutes and then allowed to stand for 30 minutes, followed by removal of the aqueous layer. This water washing process was repeated five times until the pH of the waste water became neutral. Then, the solvent in the ester layer was removed by distillation under a reduced pressure of 1 kPa at 180° C., and the resultant mixture was filtrated. Thus, an ester having a melting point of 68.9° C., an acid value of 0.4 mgKOH/g, a hydroxyl value of 3.4 mgKOH/g, and a color number (APHA) of 160 was obtained in an amount of 935.2 g, as a final product. The yield of the ester with respect to the crude esterified product that was subjected to the neutralization treatment was 93.5%.

Comparative Example 13

First, 20 g of cyclohexane were added to 1000.0 g of the crude esterified product of Example 13 (i.e., 2 parts by weight of a hydrocarbon solvent was added with respect to 100 parts by weight of the crude esterified product). Then, a 10% potassium hydroxide aqueous solution containing an amount of potassium hydroxide that corresponds to 1.5 equivalents of the acid value of this crude esterified product was added thereto, and the mixture was stirred at 80° C. for 30 minutes. Although the mixture was allowed to stand for 30 minutes, the mixture was not separated into an ester layer and an alkali aqueous layer, and the entire mixture was in an emulsion state, and the aqueous layer could not be removed. Thereafter, the ester layer was dehydrated under a reduced pressure of 1 kPa at 100° C., and was filtrated. Thus, an ester having a melting point of 65.9° C., an acid value of 0.9 mgKOH/g, a hydroxyl value of 3.4 mgKOH/g, and a color number (APHA) of 220 was obtained in an amount of 967.1 g, as a final product. The yield of the ester with respect to the crude esterified product that was subjected to the neutralization treatment was 96.7%.

Example 14

First, 400.0 g (3.77 mol) of diethylene glycol and 1770.4 g (7.76 mol) of myristic acid were put in a 3 liter four-necked flask provided with a thermometer, a nitrogen inlet tube, a stirrer and a condenser, and a reaction was conducted at atmospheric pressure under a nitrogen stream at 220° C. for 15 hours while removing water that was produced by the reaction by distillation. Thus, a crude esterified product was obtained in an amount of 2014.3 g, and the acid value thereof was 10.5 mgKOH/g. Then, 100 g of normal heptane and 180 g of ethanol were added to 1000.0 g of the crude esterified product (i.e., 10 parts by weight of a hydrocarbon solvent and 18 parts by weight of an alcohol solvent were added with respect to 100 parts by weight of the crude esterified product). Then, a 10% potassium hydroxide aqueous solution containing an amount of potassium hydroxide that corresponds to 1.5 equivalents of the acid value of this crude esterified product was added thereto, and the mixture was stirred at 70° C. for 30 minutes. This mixture was allowed to stand for 30 minutes and the aqueous layer was removed, and thus a neutralization process was completed. Then, ion exchanged water was added in an amount of 20 parts by weight with respect to 100 parts by weight of the crude esterified product, and the mixture was stirred at 70° C. for 30 minutes and then allowed to stand for 30 minutes, followed by removal of the aqueous layer. This water washing process was repeated four times until the pH of the waste water became neutral. Then, the solvent in the ester layer was removed by distillation under a reduced pressure of 1 kPa at 180° C., and the resultant mixture was filtrated. Thus, an ester having a melting point of 53.0° C., an acid value of 0.12 mgKOH/g, a hydroxyl value of 1.3 mgKOH/g, and a color number (APHA) of 60 was obtained in an amount of 936.2 g, as a final product. The yield of the ester with respect to the crude esterified product that was subjected to the neutralization treatment was 93.6%.

Comparative Example 14

An adsorption process was performed by adding 10 g of Galleon Earth V2 (manufactured by Mizusawa Chemical Industries) and 10 g of Tomita AD300P (manufactured by Tomita Pharmaceutical Co. Ltd.) to 1000.0 g of the crude esterified product of Example 14. The temperature, the pressure and the time during the adsorption process were 100° C., 1 kPa and three hours, respectively. Then, the resultant mixture was filtrated. Thus, an ester having a melting point of 50.3° C., an acid value of 10.2 mgKOH/g, a hydroxyl value of 1.3 mgKOH/g, and a color number (APHA) of 90 was obtained in an amount of 960.2 g, as a final product. The yield of the ester with respect to the crude esterified product that was subjected to the adsorption process was 96.0%.

The results of Examples 1 to 14 and Comparative Examples 1 to 14 are shown in Tables 1 to 3 below. In Tables 1 to 3 below, "Separation" shows the state of the separation of an ester layer and an aqueous layer at the time of the neutralization treatment. "○" means that the separation is satisfactory, and emulsification did not occur. "×" means that the separation is poor, or emulsification occurred. "Δ" means that an emulsified layer was formed between an oil layer and an aqueous layer, and the separation of the layers was poor. "–" means that no neutralization treatment was performed.

TABLE 1

| | | | | Properties of esters | | | | |
|---|---|---|---|---|---|---|---|---|
| | Materials | Solvent[a] (parts by weight)[b] | Separation | Yield (%) | Melting point (° C.) | Acid value (mgKOH/g) | APHA color number | Adsorbent |
| Example 1 | Pentaerythritol Stearic acid | Toluene(20) Isopropanol(26) | ○ | 95.2 | 77.3 | 0.07 | 50 | — |
| Com. Ex. 1 | Pentaerythritol Stearic acid | Toluene(2) 10% Sodium sulfate | × | 90.3 | 75.1 | 0.35 | 90 | — |
| Example 2 | Pentaerythritol Palmitic acid Stearic acid | Toluene(8) Isopropanol(10) | ○ | 94.1 | 67.7 | 0.2 | 60 | Activated clay SA-1 Activated alumina DN-1 |
| Com. Ex. 2 | Pentaerythritol Palmitic acid Stearic acid | Isopropanol(10) | × | 94.6 | 63.4 | 0.7 | 90 | Activated clay SA-1 Activated alumina DN-1 |
| Example 3 | Trimethylolpropane Lauric acid | n-Heptane(5) Ethanol(10) | ○ | 90.2 | 28.0 | 0.2 | 50 | Activated clay SA-1 Activated alumina DN-1 |
| Com. Ex. 3 | Trimethylolpropane Lauric acid | Methanol(10) | Δ | 84.3 | 24.5 | 0.4 | 90 | Activated clay SA-1 Activated alumina DN-1 |
| Example 4 | Trimethylolpropane Palmitic acid | Cyclohexane(15) Ethanol(10) | ○ | 95.1 | 45.5 | 0.4 | 60 | Kyowaad 500SH |
| Com. Ex. 4 | Trimethylolpropane Palmitic acid | Cyclohexane(1.5) 10% Sodium sulfate | × | 91.3 | 42.5 | 1.2 | 80 | Kyowaad 500SH |
| Example 5 | Trimethylolmethane Arachic acid | Xylene(10) Isopropanol(10) | ○ | 94.8 | 74.0 | 0.2 | 40 | Kyowaad 500SH |
| Com. Ex. 5 | Trimethylolmethane Arachic acid | — | — | 96.5 | 68.2 | 8.9 | 140 | Kyowaad 500SH |
| Example 6 | Glycerin Lauric acid | Cyclohexane(5) Isopropanol(10) | ○ | 92.5 | 46.4 | 0.2 | 40 | Activated clay SA-1 Activated alumina DN-1 |
| Com. Ex. 6 | Glycerin Lauric acid | 10% Sodium sulfate | × | 86.1 | 42.1 | 0.7 | 80 | Activated clay SA-1 Activated alumina DN-1 |

[a]Solvent used for neutralization
[b]Parts by weight per 100 parts by weight of crude esterified product

TABLE 2

|  | Materials | Solvent[a] (parts by weight)[b] | Separation | Yield (%) | Melting point (° C.) | Acid value (mgKOH/g) | APHA color number | Adsorbent |
|---|---|---|---|---|---|---|---|---|
| Example 7 | Dipentaerythritol Palmitic acid | Cyclohexane(23) Ethanol(12) | ○ | 88.9 | 73.2 | 0.09 | 60 | — |
| Com. Ex. 7 | Dipentaerythritol Palmitic acid | 20% Sodium sulfate | X | 84.3 | 71.8 | 0.60 | 100 | — |
| Example 8 | Behenyl alcohol Behenic acid | Toluene(13), Xylene(6) Isopropanol(3) Ethanol(24) | ○ | 95.4 | 73.0 | 0.08 | 55 | — |
| Com. Ex. 8 | Behenyl alcohol Behenic acid | — | — | 97.3 | 70.1 | 8.4 | 90 | Galleon Earth V2 Tomita AD300P |
| Example 9 | Stearyl alcohol Trimellitic acid | Toluene(10) Ethanol(12) | ○ | 94.3 | 68.2 | 0.3 | 55 | Activated clay SA-1 Activated alumina DN-1 |
| Com. Ex. 9 | Stearyl alcohol Trimellitic acid | — | — | 96.8 | 65.4 | 9.9 | 100 | Activated clay SA-1 Activated alumina DN-1 |
| Example 10 | Lauryl alcohol Terephthalic acid | Toluene(15) Isopropanol(10) | ○ | 93.6 | 68.2 | 0.2 | 70 | Activated carbon Shirasagi C |
| Com. Ex. 10 | Lauryl alcohol Terephthalic acid | Toluene(2) | X | 95.0 | 66.4 | 0.8 | 150 | Activated carbon Shirasagi C |
| Example 11 | Lauryl alcohol Terephthalic acid | Toluene(15) Isopropanol(10) | ○ | 95.2 | 68.1 | 0.4 | 140 | — |
| Com. Ex. 11 | Lauryl alcohol Terephthalic acid | Toluene(2) | X | 96.2 | 66.2 | 0.9 | 250 | — |

[a]Solvent used for neutralization
[b]Parts by weight per 100 parts by weight of crude esterified product

TABLE 3

|  | Materials | Solvent[a] (parts by weight)[b] | Separation | Yield (%) | Melting point (° C.) | Acid value (mgKOH/g) | APHA color number | Adsorbent |
|---|---|---|---|---|---|---|---|---|
| Example 12 | 1,4-Butanediol Stearic acid | Cyclohexane(20) Ethanol(10) | ○ | 91.5 | 69.0 | 0.2 | 80 | Activated carbon Shirasagi C |
| Com. Ex. 12 | 1,4-Butanediol Stearic acid | Cyclohexane(2) | X | 95.0 | 65.9 | 0.8 | 150 | Activated carbon Shirasagi C |
| Example 13 | 1,4-Butanediol Stearic acid | Cyclohexane(20) Ethanol(10) | ○ | 93.5 | 68.9 | 0.4 | 160 | — |
| Com. Ex. 13 | 1,4-Butanediol Stearic acid | Cyclohexane(2) | X | 96.7 | 65.9 | 0.9 | 220 | — |
| Example 14 | Diethylene glycol Myristic acid | n-Heptane(10) Ethanol(18) | ○ | 93.6 | 53.0 | 0.12 | 60 | — |
| Com. Ex. 14 | Diethylene glycol Myristic acid | — | — | 96.0 | 50.3 | 10.2 | 90 | Galleon Earth V2 Tomita AD300P |

[a]Solvent used for neutralization
[b]Parts by weight per 100 parts by weight of crude esterified product All of Examples 1 to 14 and Comparative Examples 1 to 14 are examples that are intended for ester waxes having a high melting point. In each of Examples 1 to 14, a good separation state was accomplished at the time of the neutralization treatment, and an ester having a low acid value, a satisfactory color number, and a high melting point was obtained. On the other hand, in each of Comparative Examples 1 to 14, emulsification or poor separation of the layers occurred at the neutralization treatment, the yield of the resultant ester was poor, and the resultant ester has a low melting point, a high acid value, and a high color number. The esters subjected to only an adsorption treatment without the neutralization treatment with alkali have a low melting point, a high acid value and a high color number.

Examples 15 to 17 among Examples 15 to 28 and Comparative Examples 15 to 17 that are described below show production examples intended for esters for working fluids, rolling oils, and cutting oils that should be of high quality. Examples 18 to 28 and Comparative Examples 18 to 28 show production examples intended for esters for special grease and esters for refrigerating machine oils that should be of high quality.

Example 15

First, 280.0 g (2.09 mol) of trimethylolpropane and 1942.1 g (6.89 mol) of oleic acid were put in a 3 liter four-necked flask provided with a thermometer, a nitrogen inlet tube, a stirrer and a condenser, and a reaction was conducted at atmospheric pressure under a nitrogen stream at 220° C. for 15 hours while removing water that was produced by the reaction by distillation. Thus, a crude esterified product was obtained in an amount of 2088.3 g, and the acid value thereof was 17.5 mgKOH/g. Then, 200 g of toluene and 150 g of isopropanol were added to 1000.0 g of the crude esterified product (i.e., 20 parts by weight of a hydrocarbon solvent and 15 parts by weight of an alcohol solvent were added with respect to 100 parts by weight of the crude esterified product). Then, a 10% potassium hydroxide aqueous solution containing an amount of potassium hydroxide that corresponds to 1.5 equivalents of the acid value of this crude esterified product was added thereto, and the mixture was stirred at 70° C. for 30 minutes. This mixture was allowed to stand for 30 minutes and the aqueous layer was removed, and thus a neutralization process was completed. Then, ion exchanged water was added in an amount of 20 parts by weight with respect to 100 parts by weight of the crude esterified product, and the mixture was stirred at 90° C. for 30 minutes and then allowed to stand for 30 minutes, followed by removal of the aqueous layer. This water washing process was repeated four times until the pH of the waste water became neutral. Then, the solvent in the ester layer was removed by distillation under a reduced pressure of 1 kPa at 180° C. Then, an adsorption process was performed by adding 5 g of Galleon Earth V2 (manufactured by Mizusawa Chemical Industries) and 5 g of Tomita AD300P (manufactured by Tomita Pharmaceutical Co. Ltd.). The temperature, the pressure and the time during the adsorption process were 100° C., 1 kPa and three hours, respectively. Then, the resultant mixture was filtrated. Thus, an ester having a kinematic viscosity (40° C.) of 64.2 mm$^2$/s, a pour point of −35° C., an acid value of 0.11 mgKOH/g, a hydroxyl value of 0.5 mgKOH/g, and a color number (APHA) of 190 was obtained in an amount of 911.7 g, as a final product. The yield of the ester with respect to the crude esterified product that was subjected to the neutralization treatment was 91.2%.

Table 4 shows the conditions for the neutralization treatment of this example, the state of the separation, and the yield and the properties of the obtained ester. Table 4 also shows such experimental data of Examples 16 to 28 and Comparative Example 15 to 28 described below.

Comparative Example 15

To 1000.0 g of the crude esterified product of Example 15, a 10% potassium hydroxide aqueous solution containing an amount of potassium hydroxide that corresponds to 1.5 equivalents of the acid value of this crude esterified product was added, and the mixture was stirred at 90° C. for 30 minutes. Although the mixture was allowed to stand for 30 minutes, the mixture was not separated into an ester layer and an alkali aqueous layer, and the entire mixture was in an emulsion state, and the aqueous layer could not be removed. Then, 200 g of 20% sodium sulfate hot water solution were added, and the mixture was stirred at 90° C. for 30 minutes and then allowed to stand for 30 minutes, followed by removal of the aqueous layer. Then, ion exchanged water was added in an amount of 20 parts by weight with respect to 100 parts by weight of the crude esterified product, and the mixture was stirred at 90° C. for 30 minutes and then allowed to stand for 30 minutes, followed by removal of the aqueous layer. This water washing process was repeated four times until the pH of the waste water became neutral. Then, the ester layer was dehydrated under a reduced pressure of 1 kPa at 90° C. Then, an adsorption process was performed by adding 5 g of Galleon Earth V2 (manufactured by Mizusawa Chemical Industries) and 5 g of Tomita AD300P (manufactured by Tomita Pharmaceutical Co. Ltd.). The temperature, the pressure and the time during the adsorption process were 100° C., 1 kPa and three hours, respectively. Then, the resultant mixture was filtrated. Thus, an ester having a kinematic viscosity (40° C.) of 64.1 mm$^2$/s, a pour point of −35° C., an acid value of 0.20 mgKOH/g, a hydroxyl value of 0.5 mgKOH/g, and a color number (APHA) of 450 was obtained in an amount of 760.7 g, as a final product. The yield of the ester with respect to the crude esterified product that was subjected to the neutralization treatment was 76.1%.

Example 16

First, 530.0 g (3.95 mol) of trimethylolpropane and 1843.0 g (12.80 mol) of caprylic acid were put in a 3 liter four-necked flask provided with a thermometer, a nitrogen inlet tube, a stirrer and a condenser, and a reaction was conducted at atmospheric pressure under a nitrogen stream at 220° C. while removing water that was produced by the reaction by distillation. The reaction was stopped when the hydroxyl value reached 3 mgKOH/g or less. Thus, a crude esterified product was obtained in an amount of 2009.5 g, and the acid value thereof was 1.5 mgKOH/g.

Then, 150 g of toluene were added to 1000.0 g of the crude esterified product (i.e., 15 parts by weight of a hydrocarbon solvent were added with respect to 100 parts by weight of the crude esterified product). Then, a 10% potassium hydroxide aqueous solution containing an amount of potassium hydroxide that corresponds to 1.5 equivalents of the acid value of this crude esterified product was added thereto, and the mixture was stirred at 70° C. for 30 minutes. This mixture was allowed to stand for 30 minutes and the aqueous layer was removed, and thus a neutralization process was completed. Then, ion exchanged water was added in an amount of 20 parts by weight with respect to 100 parts by weight of the crude esterified product, and the mixture was stirred at 70° C. for 30 minutes and then allowed to stand for 30 minutes, followed by removal of the aqueous layer. This water washing process was repeated four times until the pH of the waste water became neutral. Then, the solvent in the ester layer was removed by distillation under a reduced pressure of 1 kPa at 180° C. Then, an adsorption process was performed by adding 5 g of activated carbon Shirasagi C (manufactured by Takeda Chemical Industries, Ltd.). The temperature, the pressure and the time during the adsorption process were 100° C., 1 kPa and three hours, respectively. Then, the resultant mixture was filtrated. Thus, an ester having a kinematic viscosity (40° C.) of 16.7 mm$^2$/s, a pour point of −50° C. or less, an acid value of 0.12 mgKOH/g, a hydroxyl value of 0.5 mgKOH/g, and a color number (APHA) of 50 was obtained in an amount of 915.1 g, as a final product. The yield of the ester with respect to the crude esterified product that was subjected to the neutralization treatment was 91.5%.

Comparative Example 16

To 1000.0 g of the crude esterified product of Example 16, a 10% potassium hydroxide aqueous solution containing an amount of potassium hydroxide that corresponds to 1.5 equivalents of the acid value of this crude esterified product was added, and the mixture was stirred at 90° C. for 30 minutes. When the mixture was allowed to stand for 30 minutes, an emulsified layer was formed between an ester layer and an alkali aqueous layer, and the mixture was still allowed to stand for further 30 minutes. Then, the aqueous layer was removed. The resultant mixture was washed with water four times until the pH of the waste water became neutral. Then, the ester layer was dehydrated under a reduced pressure of 1 kPa at 100° C.

Then, an adsorption process was performed by adding 5 g of activated carbon Shirasagi C (manufactured by Takeda Chemical Industries, Ltd.). The temperature, the pressure and the time during the adsorption process were 100° C., 1 kPa and three hours, respectively. Then, the resultant mixture was filtrated. Thus, an ester having a kinematic viscosity (40° C.) of 16.7 mm$^2$/s, a pour point of −50° C. or less, an acid value of 0.16 mgKOH/g, a hydroxyl value of 0.5 mgKOH/g, and a color number (APHA) of 60 was obtained in an amount of 901.2 g, as a final product. The yield of the ester with respect to the crude esterified product that was subjected to the neutralization treatment was 90.1%.

Example 17

First, 380.0 g (2.83 mol) of trimethylolpropane, 1184.4 g (4.27 mol) of oleic acid, and 806.6 g (1.40 mol) of dimmer acid were put in a 3 liter four-necked flask provided with a thermometer, a nitrogen inlet tube, a stirrer and a condenser, and a reaction was conducted at atmospheric pressure under a nitrogen stream at 220° C. for 12 hours while removing water that was produced by the reaction by distillation. Thus, a crude esterified product was obtained in an amount of 2203.5 g, and the acid value thereof was 3.8 mgKOH/g.

Then, 100 g of normal heptane were added to 1000.0 g of the crude esterified product (i.e., 10 parts by weight of a hydrocarbon solvent were added with respect to 100 parts by weight of the crude esterified product). Then, a 10% potassium hydroxide aqueous solution containing an amount of potassium hydroxide that corresponds to 1.5 equivalents of the acid value of this crude esterified product was added thereto, and the mixture was stirred at 70° C. for 30 minutes. This mixture was allowed to stand for 30 minutes and the aqueous layer was removed, and thus a neutralization process was completed. Then, ion exchanged water was added in an amount of 20 parts by weight with respect to 100 parts by weight of the crude esterified product, and the mixture was stirred at 70° C. for 30 minutes and then allowed to stand for 30 minutes, followed by removal of the aqueous layer. This water washing process was repeated four times until the pH of the waste water became neutral. Then, the solvent in the ester layer was removed by distillation under a reduced pressure of 1 kPa at 180° C. Then, an adsorption process was performed by adding 5 g of Kyowaad 500SH (manufactured by Kyowa Chemical Industry Co., Ltd). The temperature, the pressure and the time during the adsorption process were 100° C., 1 kPa and three hours, respectively. Then, the resultant mixture was filtrated. Thus, an ester having a kinematic viscosity (40° C.) of 540.6 mm$^2$/s, a pour point of −35° C., an acid value of 0.6 mgKOH/g, a hydroxyl value of 15.5 mgKOH/g, and a color number (APHA) of 210 was obtained in an amount of 934.2 g, as a final product. The yield of the ester with respect to the crude esterified product that was subjected to the neutralization treatment was 93.4%.

Comparative Example 17

An adsorption process was performed by adding 5 g of Kyowaad 500SH (manufactured by Kyowa Chemical Industry Co., Ltd) to 1000.0 g of the crude esterified product of Example 17. The temperature, the pressure and the time during the adsorption process were 100° C., 1 kPa and three hours, respectively. Then, the resultant mixture was filtrated. Thus, an ester having a kinematic viscosity (40° C.) of 521.2 mm$^2$/s, a pour point of −35° C., an acid value of 3.6 mgKOH/g, a hydroxyl value of 15.5 mgKOH/g, and a color number (APHA) of 300 was obtained in an amount of 989.1 g, as a final product. The yield of the ester with respect to the crude esterified product that was subjected to the neutralization treatment was 98.9%.

Example 18

First, 800.0 g (5.96 mol) of trimethylolpropane, 1052.1 g (7.31 mol) of caprylic acid, 406.1 g (2.36 mol) of capric acid, and 560.6 g (3.84 mol) of adipic acid were put in a 3 liter four-necked flask provided with a thermometer, a nitrogen inlet tube, a stirrer and a condenser, and a reaction was conducted at atmospheric pressure under a nitrogen stream at 220° C. for 12 hours while removing water that was produced by the reaction by distillation. After the reaction was stopped, unreacted fatty acids were removed by distillation under a reduced pressure of 1 kPa. Thus, a crude esterified product was obtained in an amount of 2082.6 g, and the acid value thereof was 5.5 mgKOH/g.

Then, 200 g of xylene and 50 g of ethanol were added to 1000.0 g of the crude esterified product (i.e., 20 parts by weight of a hydrocarbon solvent and 5 parts by weight of an alcohol solvent were added with respect to 100 parts by weight of the crude esterified product). Then, a 10% potassium hydroxide aqueous solution containing an amount of potassium hydroxide that corresponds to 1.5 equivalents of the acid value of this crude esterified product was added thereto, and the mixture was stirred at 70° C. for 30 minutes. This mixture was allowed to stand for 30 minutes and the aqueous layer was removed, and thus a neutralization process was completed. Then, ion exchanged water was added in an amount of 20 parts by weight with respect to 100 parts by weight of the crude esterified product, and the mixture was stirred at 70° C. for 30 minutes and then allowed to stand for 30 minutes, followed by removal of the aqueous layer. This water washing process was repeated four times until the pH of the waste water became neutral. Then, the solvent in the ester layer was removed by distillation under a reduced pressure of 1 kPa at 180° C., and the resultant mixture was filtrated. Thus, an ester having a kinematic viscosity (40° C.) of 245.1 mm$^2$/s, a pour point of −32.5° C., an acid value of 0.5 mgKOH/g, a hydroxyl value of 20.2 mgKOH/g, and a color number (APHA) of 80 was obtained in an amount of 943.3 g, as a final product. The yield of the ester with respect to the crude esterified product that was subjected to the neutralization treatment was 94.3%.

Comparative Example 18

First, 20 g of xylene were added to 1000.0 g of the crude esterified product of Example 18 (i.e., 2 parts by weight of a hydrocarbon solvent was added with respect to 100 parts by weight of the crude esterified product). A 10% potassium hydroxide aqueous solution containing an amount of potassium hydroxide that corresponds to 1.5 equivalents of the acid value of this crude esterified product was added thereto, and the mixture was stirred at 90° C. for 30 minutes. When the mixture was allowed to stand for 30 minutes, an oil layer and an aqueous layer were formed, but these layers were partially emulsified. Then, 100 g of 10% sodium sulfate hot water solution were added, and the mixture was then allowed to stand for further 30 minutes, followed by removal of the aqueous layer. The mixture was washed with water four times until the pH of the waste water became neutral. Then, the solvent in the ester layer was removed by distillation under a reduced pressure of 1 kPa at 180° C., and the resultant mixture was filtrated. Thus, an ester having a kinematic viscosity (4°° C.) of 240.0 mm$^2$/s, a pour point of −35.0° C., an acid value of 0.8 mgKOH/g, a hydroxyl value of 20.2 mgKOH/g, and a color number (APHA) of 100 was obtained in an amount of 919.2 g, as a final product. The yield of the ester with respect to the crude esterified product that was subjected to the neutralization treatment was 91.9%.

Example 19

First, 500.0 g (1.97 mol) of dipentaerythritol, 917.2 g (6.37 mol) of 2-ethylhexanoic acid, 1000.0 g (6.37 mol) of 3,5,5-trimethylhexanoic acid and 2.1 g of stannic oxide were put in a 3 liter four-necked flask provided with a thermometer, a nitrogen inlet tube, a stirrer and a condenser, and a reaction was conducted at atmospheric pressure under a nitrogen stream at 220° C. for 15 hours while removing water that was produced by the reaction by distillation. After the reaction was stopped, unreacted fatty acids were removed by distillation under a reduced pressure of 1 kPa. Thus, a crude esterified product was obtained in an amount of 2020.9 g, and the acid value thereof was 0.8 mgKOH/g.

Then, 100 g of toluene were added to 1000.0 g of the crude esterified product (i.e., 10 parts by weight of a hydrocarbon solvent were added with respect to 100 parts by weight of the crude esterified product). Then, a 10% potassium hydroxide aqueous solution containing an amount of potassium hydroxide that corresponds to 1.5 equivalents of the acid value of this crude esterified product was added thereto, and the mixture was stirred at 70° C. for 30 minutes. This mixture was allowed to stand for 30 minutes and the aqueous layer was removed, and thus a neutralization process was completed. Then, ion exchanged water was added in an amount of 20 parts by weight with respect to 100 parts by weight of the crude esterified product, and the mixture was stirred at 70° C. for 30 minutes and then allowed to stand for 30 minutes, followed by removal of the aqueous layer. This water washing process was repeated four times until the pH of the waste water became neutral. Then, the solvent in the ester layer was removed by distillation under a reduced pressure of 1 kPa at 180° C. Then, an adsorption process was performed by adding 5 g of activated clay SA-1 (manufactured by Nihon Kassei Hakudo) and 5 g of activated alumina DN-1A (manufactured by Mizusawa Chemical Industries). The temperature, the pressure and the time during the adsorption process were 100° C., 1 kPa and three hours, respectively. Then, the resultant mixture was filtrated. Thus, an ester having a kinematic viscosity (40° C.) of 227.6 $mm^2/s$, a pour point of −40° C., an acid value of 0.01 mgKOH/g, a hydroxyl value of 0.1 mgKOH/g, and a color number (APHA) of 90 was obtained in an amount of 926.1 g, as a final product. The yield of the ester with respect to the crude esterified product that was subjected to the neutralization treatment was 92.6%.

Comparative Example 19

First, 20 g of toluene were added to 1000.0 g of the crude esterified product of Example 19 (i.e., 2 parts by weight of a hydrocarbon solvent was added with respect to 100 parts by weight of the crude esterified product). A 10% potassium hydroxide aqueous solution containing an amount of potassium hydroxide that corresponds to 1.5 equivalents of the acid value of this crude esterified product was added thereto, and the mixture was stirred at 90° C. for 30 minutes. When the mixture was allowed to stand for 30 minutes, an oil layer and an aqueous layer were formed, but these layers were partially emulsified. Thereafter, the mixture was still allowed to stand for further 30 minutes, followed by removal of the aqueous layer. The resultant mixture was washed with water four times until the pH of the waste water became neutral. Then, the ester layer was dehydrated under a reduced pressure of 1 kPa at 100° C. Then, an adsorption process was performed by adding 10 g of activated clay SA-1 (manufactured by Nihon Kassei Hakudo) and 10 g of activated alumina DN-1A (manufactured by Mizusawa Chemical Industries). The temperature, the pressure and the time during the adsorption process were 100° C., 1 kPa, and three hours, respectively. Then, the resultant mixture was filtrated. Thus, an ester having a kinematic viscosity (40° C.) of 227.1 $mm^2/s$, a pour point of −40° C., an acid value of 0.01 mgKOH/g, a hydroxyl value of 0.1 mgKOH/g, and a color number (APHA) of 150 was obtained in an amount of 884.2 g, as a final product. The yield of the ester with respect to the crude esterified product that was subjected to the neutralization treatment was 88.4%.

Example 20

First, 520.0 g (2.04 mol) of dipentaerythritol and 1943.4 g (13.50 mol) of 2-ethylhexanoic acid were put in a 3 liter four-necked flask provided with a thermometer, a nitrogen inlet tube, a stirrer and a condenser, and a reaction was conducted at atmospheric pressure under a nitrogen stream at 220° C. for 15 hours while removing water that was produced by the reaction by distillation. After the reaction was stopped, unreacted fatty acid (2-ethylhexanoic acid) was removed by distillation under a reduced pressure of 1 kPa.

Thus, a crude esterified product was obtained in an amount of 2048.2 g, and the acid value thereof was 1.2 mgKOH/g. Then, 200 g of toluene were added to 1000.0 g of the crude esterified product (i.e., 20 parts by weight of a hydrocarbon solvent were added with respect to 100 parts by weight of the crude esterified product). Then, a 10% potassium hydroxide aqueous solution containing an amount of potassium hydroxide that corresponds to 1.5 equivalents of the acid value of this crude esterified product was added thereto, and the mixture was stirred at 70° C. for 30 minutes. This mixture was allowed to stand for.30 minutes and the aqueous layer was removed, and thus a neutralization process was completed. Then, ion exchanged water was added in an amount of 20 parts by weight with respect to 100 parts by weight of the crude esterified product, and the mixture was stirred at 90° C. for 30 minutes and then allowed to stand for 30 minutes, followed by removal of the aqueous layer. This water washing process was repeated four times until the pH of the waste water became neutral. Then, the solvent in the ester layer was removed by distillation under a reduced pressure of 1 kPa at 180° C. Then, an adsorption process was performed by adding 5 g of Galleon Earth V2 (manufactured by Mizusawa Chemical Industries) and 5 g of Tomita AD300P (manufactured by Tomita Pharmaceutical Co. Ltd.). The temperature, the pressure and the time during the adsorption process were 100° C., 1 kPa and three hours, respectively. Then, the resultant mixture was filtrated. Thus, an ester having a kinematic viscosity (40° C.) of 143.6 $mm^2/s$, a pour point of −40° C., an acid value of 0.01 mgKOH/g, a hydroxyl value of 0.4 mgKOH/g, and a color number (APHA) of 60 was obtained in an amount of 949.3 g, as a final product. The yield of the ester with respect to the crude esterified product that was subjected to the neutralization treatment was 94.9%.

Comparative Example 20

First, 25 g of toluene were added to 1000.0 g of the crude esterified product of Example 20 (i.e., 2.5 parts by weight of a hydrocarbon solvent was added with respect to 100 parts by weight of the crude esterified product). Then, a 10% potassium hydroxide aqueous solution containing an amount of potassium hydroxide that corresponds to 1.5 equivalents of the acid value of this crude esterified product was added thereto, and the mixture was stirred at 90° C. for 30 minutes. Although the mixture was allowed to stand for 30 minutes, the mixture was not separated into an ester layer and an alkali aqueous layer, and the entire mixture was in an emulsion state, and the aqueous layer could not be removed.

Then, 250 g of 10% sodium sulfate hot water solution were added, and the mixture was stirred at 90° C. for 30 minutes and then allowed to stand for 30 minutes, followed by removal of the aqueous layer. Then, ion exchanged water was added in an amount of 20 parts by weight with respect to 100 parts by weight of the crude esterified product, and the mixture was stirred at 90° C. for 30 minutes and then allowed to stand for 30 minutes, followed by removal of the aqueous layer. This water washing process was repeated four times until the pH of the waste water became neutral. Then, the solvent in the ester layer was removed by distillation under a reduced pressure of 1 kPa at 180° C. Then, an adsorption process was performed by adding 5 g of Galleon Earth V2 (manufactured by Mizusawa Chemical Industries) and 5 g of Tomita AD300P (manufactured by Tomita Pharmaceutical Co. Ltd.). The temperature, the pressure and the time during the adsorption process were 100° C., 1 kPa and three hours, respectively. Then, the resultant mixture was filtrated. Thus, an ester having a kinematic viscosity (40° C.) of 143.6 mm$^2$/s, a pour point of −40° C., an acid value of 0.01 mgKOH/g, a hydroxyl value of 0.4 mgKOH/g, and a color number (APHA) of 120 was obtained in an amount of 863.0 g, as a final product. The yield of the ester with respect to the crude esterified product that was subjected to the neutralization treatment was 86.3%.

Example 21

First, 900.0 g (8.64 mol) of neopentylglycol, 694.2 g (5.34 mol) of n-heptanoic acid and 909.6 g (6.23 mol) of adipic acid were put in a 3 liter four-necked flask provided with a thermometer, a nitrogen inlet tube, a stirrer and a condenser, and a reaction was conducted at atmospheric pressure under a nitrogen stream at 220° C. for 15 hours while removing water that was produced by the reaction by distillation. After the reaction was stopped, unreacted fatty acids (n-heptanoic acid and adipic acid) were removed by distillation under a reduced pressure of 5 kPa. Thus, a crude esterified product was obtained in an amount of 2083.2 g, and the acid value thereof was 4.3 mgKOH/g.

Then, 200 g of xylene I were added to 1000.0 g of the crude esterified product (i.e., 20 parts by weight of a hydrocarbon solvent were added with respect to 100 parts by weight of the crude esterified product). Then, a 10% potassium hydroxide aqueous solution containing an amount of potassium hydroxide that corresponds to 1.5 equivalents of the acid value of this crude esterified product was added thereto, and the mixture was stirred at 70° C. for 30 minutes. This mixture was allowed to stand for 30 minutes and the aqueous layer was removed, and thus a neutralization process was completed. Then, ion exchanged water was added in an amount of 20 parts by weight with respect to 100 parts by weight of the crude esterified product, and the mixture was stirred at 90° C. for 30 minutes and then allowed to stand for 30 minutes, followed by removal of the aqueous layer. This water washing process was repeated four times until the pH of the waste water became neutral. Then, the solvent in the ester layer was removed by distillation under a reduced pressure of 1 kPa at 180° C. Then, an adsorption process was performed by adding 5 g of Galleon Earth V2 (manufactured by Mizusawa Chemical Industries) and 5, g of Tomita AD300P (manufactured by Tomita Pharmaceutical Co. Ltd.). The temperature, the pressure and the time during the adsorption process were 100° C., 1 kPa and three hours, respectively. Then, the resultant mixture was filtrated. Thus, an ester having a kinematic viscosity (40° C.) of 267.5 mm$^2$/s, a pour point of −50° C. or less, an acid value of 0.01 mgKOH/g, a hydroxyl value of 0.6 mgKOH/g, and a color number (APHA) of 30 was obtained in an amount of 956.5 g, as a final product. The yield of the ester with respect to the crude esterified product that was subjected to the neutralization treatment was 95.7%.

Comparative Example 21

To 1000.0 g of the crude esterified product of Example 21, a 10% potassium hydroxide aqueous solution containing an amount of potassium hydroxide that corresponds to 1.5 equivalents of the acid value of this crude esterified product was added, and the mixture was stirred at 90° C. for 30 minutes. Although the mixture was allowed to stand for 30 minutes, the mixture was not separated into an ester layer and an alkali aqueous layer, and the entire mixture was in an emulsion state, and the aqueous layer could not be removed. Then, 300 g of 10% sodium sulfate hot water solution were added, and the mixture was stirred at 90° C. for 30 minutes and then allowed to stand for 30 minutes, followed by removal of the aqueous layer. Then, ion exchanged water was added in an amount of 20 parts by weight with respect to 100 parts by weight of the crude esterified product, and the mixture was stirred at 90° C. for 30 minutes and then allowed to stand for 30 minutes, followed by removal of the aqueous layer. This water washing process was repeated four times until the pH of the waste water became neutral. Then, the ester layer was dehydrated under a reduced pressure of 1 kPa at 90° C. Then, an adsorption process was performed by adding 5 g of Galleon Earth V2 (manufactured by Mizusawa Chemical Industries) and 5 g of Tomita AD300P (manufactured by Tomita Pharmaceutical Co. Ltd.). The temperature, the pressure and the time during the adsorption process were 100° C., 1 kPa and three hours, respectively. Then, the resultant mixture was filtrated. Thus, an ester having a kinematic viscosity (40° C.) of 267.5 mm$^2$/s, a pour point of −50° C. or less, an acid value of 0.01 mgKOH/g, a hydroxyl value of 0.6 mgKOH/g, and a color number (APHA) of 70 was obtained in an amount of 950.8 g, as a final product. The yield of the ester with respect to the crude esterified product that was subjected to the neutralization treatment was 95.1%.

Example 22

First, 610.0 g (5.86 mol) of neopentylglycol and 1771.0 g (12.30 mol) of 2-ethylhexanoic acid were put in a 3 liter four-necked flask provided with a thermometer, a nitrogen inlet tube, a stirrer and a condenser, and a reaction was conducted at atmospheric pressure under a nitrogen stream at 220° C. while removing water that was produced by the reaction by distillation. The reaction was stopped when the hydroxyl value reached 3 mgKOH/g or less. After the reaction was stopped, unreacted fatty acid was removed by distillation under a reduced pressure of 1 kPa. Thus, a crude esterified product was obtained in an amount of 2026.8 g, and the acid value thereof was 1.8 mgKOH/g.

Then, 80 g of toluene were added to 1000.0 g of the crude esterified product (i.e., 8 parts by weight of a hydrocarbon solvent were added with respect to 100 parts by weight of the crude esterified product). Then, a 10% potassium hydroxide aqueous solution containing an amount of potassium hydroxide that corresponds to 1.5 equivalents of the acid value of this crude esterified product was added thereto, and the mixture was stirred at 70° C. for 30 minutes. This mixture was allowed to stand for 30 minutes and the aqueous layer was removed, and thus a neutralization process was completed. Then, ion exchanged water was added in an amount of 20 parts by weight with respect to 100 parts by weight of the crude esterified product, and the mixture was stirred at 70° C. for 30 minutes and then allowed to stand for 30 minutes, followed by removal of the aqueous layer. This water washing process was repeated four times until the pH of the waste water became neutral. Then, the solvent in the ester layer was removed by distillation under a reduced pressure of 1 kPa at 180° C. Then, the obtained ester was distilled at 180° C., a pressure in the range of 10 to 500 Pa, and a flow rate of 4 mL/min with a Smith type distillatory. Thus, an ester having a kinematic viscosity (40° C.) of 7.4 mm$^2$/s, a pour point of −50° C. or less, an acid value of 0.01 mgKOH/g or less, a hydroxyl value of 0.1 mgKOH/g, and a color number (APHA) of 40 was obtained in an amount of 825.1 g, as a final product. The yield of the ester with respect to the crude esterified product that had been subjected to the neutralization treatment was 82.5%.

Comparative Example 22

To 1000.0 g of the crude esterified product of Example 22, a 10% potassium hydroxide aqueous solution containing an amount of potassium hydroxide that corresponds to 1.5 equivalents of the acid value of this crude esterified product was added, and the mixture was stirred at 90° C. for 30 minutes. When the mixture was allowed to stand for 30 minutes, an oil layer and an aqueous layer were formed, but these layers were partially emulsified. Thereafter, the mixture was still allowed to stand for further 30 minutes, followed by removal of the aqueous layer. The resultant mixture was washed with water four times until the pH of the waste water became neutral. Then, the ester layer was dehydrated under a reduced pressure of 1 kPa at 100° C. Then, the obtained ester was distilled at 180° C., a pressure in the range of 10 to 500 Pa, and a flow rate of 4 mL/min with a Smith type distillatory. Thus, an ester having a kinematic viscosity (40° C.) of 7.4 mm$^2$/s, a pour point of −50° C. or less, an acid value of 0.01 mgKOH/g or less, a hydroxyl value of 0.1 mgKOH/g, and a color number (APHA) of 50 was obtained in an amount of 810.2 g, as a final product. The yield of the ester with respect to the crude esterified product that had been subjected to the neutralization treatment was 81.0%.

Example 23

First, 610.0 g (5.86 mol) of neopentylglycol and 1771.0 g (12.30 mol) of 2-ethylhexanoic acid were put in a 3 liter four-necked flask provided with a thermometer, a nitrogen inlet tube, a stirrer and a condenser, and a reaction was conducted at atmospheric pressure under a nitrogen stream at 220° C. while removing water that was produced by the reaction by distillation. The reaction was stopped when the hydroxyl value reached 3 mgKOH/g or less. After the reaction was stopped, unreacted fatty acid was removed by distillation under a reduced pressure of 1 kPa. Thus, a crude esterified product was obtained in an amount of 2026.8 g, and the acid value thereof was 1.8 mgKOH/g.

Then, 80 g of toluene were added to 1000.0 g of the crude esterified product (i.e., 8 parts by weight of a hydrocarbon solvent were added with respect to 100 parts by weight of the crude esterified product). Then, a 10% potassium hydroxide aqueous solution containing an amount of potassium hydroxide that corresponds to 1.5 equivalents of the acid value of this crude esterified product was added thereto, and the mixture was stirred at 70° C. for 30 minutes. This mixture was allowed to stand for 30 minutes and the aqueous layer was removed, and thus a neutralization process was completed. Then, ion exchanged water was added in an amount of 20 parts by weight with respect to 100 parts by weight of the crude esterified product, and the mixture was stirred at 70° C. for 30 minutes and then allowed to stand for 30 minutes, followed by removal of the aqueous layer. This water washing process was repeated four times until the pH of the waste water became neutral. Then, the solvent in the ester layer was removed by distillation under a reduced pressure of 1 kPa at 180° C. Then, an adsorption process was performed by adding 5 g of Kyowaad 500SH (manufactured by Kyowa Chemical Industry Co., Ltd). The temperature, the pressure and the time during the adsorption process were 100° C., 1 kPa and three hours, respectively. Thus, an ester having a kinematic viscosity (40° C.) of 7.4 mm$^2$/s, a pour point of −50° C. or less, an acid value of 0.01 mgKOH/g or less, a hydroxyl value of 0.1 mgKOH/g, and a color number (APHA) of 50 was obtained in an amount of 935.1 g, as a final product. The yield of the ester with respect to the crude esterified product that was subjected to the neutralization treatment was 93.5%.

Comparative Example 23

To 1000.0 g of the crude esterified product of Example 23, a 10% potassium hydroxide aqueous solution containing an amount of potassium hydroxide that corresponds to 1.5 equivalents of the acid value of this crude esterified product was added, and the mixture was stirred at 90° C. for 30 minutes. When the mixture was allowed to stand for 30 minutes, an oil layer and an aqueous layer were formed, but these layers were partially emulsified. Thereafter, the mixture was still allowed to stand for further 30 minutes, followed by removal of the aqueous layer. The resultant mixture was washed with water four times until the pH of the waste water became neutral. Then, the solvent in the ester layer was removed by distillation under a reduced pressure of 1 kPa at 180° C. Then, an adsorption process was performed by adding 5 g of Kyowaad 500SH (manufactured by Kyowa Chemical Industry Co., Ltd). The temperature, the pressure and the time during the adsorption process were 100° C., 1 kPa and three hours, respectively. Then, the resultant mixture was filtrated. Thus, an ester having a kinematic viscosity (40° C.) of 7.4 mm$^2$/s, a pour point of −50° C. or less, an acid value of 0.01 mgKOH/g, a hydroxyl value of 0.1 mgKOH/g, and a color number (APHA) of 60 was obtained in an amount of 900.2 g, as a final product. The yield of the ester with respect to the crude esterified product that was subjected to the neutralization treatment was 90.0%.

Example 24

First, 250.0 g (1.84 mol) of pentaerythritol, 883.0 g (6.13 mol) of 2-ethylhexanoic acid, 962.7 g (6.13 mol) of 3,5,5-trimethylhexanoic acid and 1.5 g (0.01 mol) of sodium hypophosphite were put in a 3 liter four-necked flask provided with a thermometer, a nitrogen inlet tube, a stirrer and a condenser, and a reaction was conducted at atmospheric pressure under a nitrogen stream at 220° C. while removing water that was produced by the reaction by distillation. The reaction was stopped when the hydroxyl value reached 3 mgKOH/g or less. After the reaction was stopped, unreacted fatty acids were removed by distillation under a reduced pressure of 1 kPa. Thus, a crude esterified product was obtained in an amount of 2051.9 g, and the acid value thereof was 1.4 mgKOH/g.

Then, 100 g of toluene were added to 1000.0 g of the crude esterified product (i.e., 10 parts by weight of a hydrocarbon solvent were added with respect to 100 parts by weight of the crude esterified product). Then, a 10% potassium hydroxide aqueous solution containing an amount of potassium hydroxide that corresponds to 1.5 equivalents of the acid value of this crude esterified product was added thereto, and the mixture was stirred at 70° C. for 30 minutes. This mixture was allowed to stand for 30 minutes and the aqueous layer was removed, and thus a neutralization process was completed. Then, ion exchanged water was added in an amount of 20 parts by weight with respect to 100 parts by weight of the crude esterified product, and the mixture was stirred at 70° C. for 30 minutes and then allowed to stand for 30 minutes, followed by removal of the aqueous layer. This water washing process was repeated four times until the pH of the waste water became neutral. Then, the solvent in the ester layer was removed by distillation under a reduced pressure of 1 kPa at 180° C. Then, an adsorption process was performed by adding 5 g of Kyowaad 500SH (manufactured by Kyowa Chemical Industry Co., Ltd). The temperature, the pressure and the time during the adsorption process were 100° C., 1 kPa and three hours, respectively. Then, the resultant mixture was filtrated. Thus, an ester having a kinematic viscosity (40° C.) of 69.2 $mm^2/s$, a pour point of –40° C., an acid value of 0.01 mgKOH/g, a hydroxyl value of 0.5 mgKOH/g, and a color number (APHA) of 40 was obtained in an amount of 925.1 g, as a final product. The yield of the ester with respect to the crude esterified product that was subjected to the neutralization treatment was 92.5%.

Comparative Example 24

To 1000.0 g of the crude esterified product of Example 24, a 10% potassium hydroxide aqueous solution containing an amount of potassium hydroxide that corresponds to 1.5 equivalents of the acid value of this crude esterified product was added, and the mixture was stirred at 90° C. for 30 minutes. When the mixture was allowed to stand for 30 minutes, an oil layer and an aqueous layer were formed, but these layers were partially emulsified. Thereafter, the mixture was still allowed to stand for further 30 minutes, followed by removal of the aqueous layer. The resultant mixture was washed with water four times until the pH of the waste water became neutral. Then, the ester layer was dehydrated under a reduced pressure of 1 kPa at 100° C. Then, an adsorption process was performed by adding 5 g of Kyowaad 500SH (manufactured by Kyowa Chemical Industry Co., Ltd). The temperature, the pressure and the time during the adsorption process were 100° C., 1 kPa and three hours, respectively. Then, the resultant mixture was filtrated. Thus, an ester having a kinematic viscosity (40° C.) of 69.2 $mm^2/s$, a pour point of –40° C., an acid value of 0.01 mgKOH/g, a hydroxyl value of 0.5 mgKOH/g, and a color number (APHA) of 60 was obtained in an amount of 912.1 g, as a final product. The yield of the ester with respect to the crude esterified product that was subjected to the neutralization treatment was 91.2%.

Example 25

First, 350.0 g (3.30 mol) of pentaerythritol, 1057.3 g (7.34 mol) of 2-ethylhexanoic acid, 797.9 g (5.54 mol) of caprylic acid, 166.8 g (0.97 mol) of capric acid, 2.6 g of titanium tetraisopropoxide, and 1.4 g (0.01 mol) of sodium hypophosphite were put in a 3 liter four-necked flask provided with a thermometer, a nitrogen inlet tube, a stirrer and a condenser, and a reaction was conducted at atmospheric pressure under a nitrogen stream at 220° C. while removing water that was produced by the reaction by distillation. The reaction was stopped when the hydroxyl value reached 3 mgKOH/g or less. After the reaction was stopped, unreacted fatty acids were removed by distillation under a reduced pressure of 1 kPa. Thus, a crude esterified product was obtained in an amount of 2009.4 g, and the acid value thereof was 2.1 mgKOH/g.

Then, 150 g of cyclohexane were added to 1000.0 g of the crude esterified product (i.e., 15 parts by weight of a hydrocarbon solvent were added with respect to 100 parts by weight of the crude esterified product). Then, a 10% potassium hydroxide aqueous solution containing an amount of potassium hydroxide that corresponds to 1.5 equivalents of the acid value of this crude esterified product was added thereto, and the mixture was stirred at 70° C. for 30 minutes. This mixture was allowed to stand for 30 minutes and the aqueous layer was removed, and thus a neutralization process was completed. Then, ion exchanged water was added in an amount of 20 parts by weight with respect to 100 parts by weight of the crude esterified product, and the mixture was stirred at 70° C. for 30 minutes and then allowed to stand for 30 minutes, followed by, removal of the aqueous layer. This water washing process was repeated four times until the pH of the waste water became neutral. Then, the solvent in the ester layer was removed by distillation under a reduced pressure of 1 kPa at 180° C. Then, an adsorption process was performed by adding 5 g of activated clay SA-1 (manufactured by Nihon Kassei Hakudo) and 5 g of activated alumina DN-1A (manufactured by Mizusawa Chemical Industries). The temperature, the pressure and the time during the adsorption process were 100° C., 1 kPa and three hours, respectively. Then, the resultant mixture was filtrated. Thus, an ester having a kinematic viscosity (40° C.) of 33.4 $mm^2/s$, a pour point of –40° C., an acid value of 0.11 mgKOH/g; a hydroxyl value of 2.1 mgKOH/g; and a color number (APHA) of 60 was obtained in an amount of 915.0 g, as a final product. The yield of the ester with respect to the crude esterified product that was subjected to the neutralization treatment was 91.5%.

Comparative Example 25

To 1000.0 g of the crude esterified product of Example 25, a 10% potassium hydroxide aqueous solution containing an amount of potassium hydroxide that corresponds to 1.5 equivalents of the acid value of this crude esterified product was added, and the mixture was stirred at 90° C. for 30 minutes. When the mixture was allowed to stand for 30 minutes, an oil layer and an aqueous layer were formed, but these layers were partially emulsified. Then, 250 g of 10% sodium sulfate hot water solution were added, and the mixture was stirred at 90° C. for 30 minutes, and the mixture was then allowed to stand for further 30 minutes, followed by removal of the aqueous layer. The resultant mixture was washed with water four times. Then, the ester layer was dehydrated under a reduced pressure of 1 kPa at 180° C. Then, an adsorption process was performed by adding 5 g of activated clay SA-1 (manufactured by Nihon Kassei Hakudo) and 5 g of activated alumina DN-1A (manufactured by Mizusawa Chemical Industries). The temperature, the pressure and the time during the adsorption process were 100° C., 1 kPa and three hours, respectively. Then, the resultant mixture was filtrated. Thus, an ester having a kinematic viscosity (40° C.) of 33.4 $mm^2/s$, a pour point of –40° C., an acid value of 0.15 mgKOH/g or less, a hydroxyl value of 2.1 mgKOH/g, and a color number (APHA) of 70 was obtained in an amount of 904.0 g, as a final product. The yield of the ester with respect to the crude esterified product that was subjected to the neutralization treatment was 90.4%.

Example 26

First, 400.0 g (2.94 mol) of pentaerythritol and 2078.8 g (13.16 mol) of 3,5,5-trimethylhexanoic acid were put in a 3 liter four-necked flask provided with a thermometer, a nitrogen inlet tube, a stirrer and a condenser, and a reaction was conducted at atmospheric pressure under a nitrogen stream at 220° C. for 15 hours while removing water that was produced by the reaction by distillation. After the reaction was stopped, unreacted fatty acid was removed by distillation under a reduced pressure of 1 kPa. Thus, a crude esterified product was obtained in an amount of 2040.2 g, and the acid value thereof was 0.8 mgKOH/g.

Then, 100 g of toluene were added to 1000.0 g of the crude esterified product (i.e., 10 parts by weight of a hydrocarbon solvent were added with respect to 100 parts by weight of the crude esterified product). Then, a 10% sodium hydroxide aqueous solution containing an amount of sodium hydroxide that corresponds to 1.5 equivalents of the acid value of this crude esterified product was added thereto, and the mixture was stirred at 70° C. for 30 minutes. This mixture was allowed to stand for 30 minutes and the aqueous layer was removed, and thus a neutralization process was completed. Then, ion exchanged water was added in an amount of 20 parts by weight with respect to 100 parts by weight of the crude esterified product, and the mixture was stirred at 90° C. for 30 minutes and then allowed to stand for 30 minutes, followed by removal of the aqueous layer. This water washing process was repeated four times until the pH of the waste water became neutral. Then, the solvent in the ester layer was removed by distillation under a reduced pressure of 1 kPa at 180° C. Then, an adsorption process was performed by adding 5 g of Galleon Earth V2 (manufactured by Mizusawa Chemical Industries) and 5 g of Tomita AD300P (manufactured by Tomita Pharmaceutical Co. Ltd.). The temperature, the pressure and the time during the adsorption process were 100° C., 1 kPa and three hours, respectively. Then, the resultant mixture was filtrated. Thus, an ester having a kinematic viscosity (40° C.) of 104.8 mm$^2$/s, a pour point of −20° C., an acid value of 0.01 mgKOH/g, a hydroxyl value of 0.8 mgKOH/g, and a color number (APHA) of 35 was obtained in an amount of 954.7 g, as a final product. The yield of the ester with respect to the crude esterified product that was subjected to the neutralization treatment was 95.5%.

Comparative Example 26

First, 15 g of toluene were added to 1000.0 g of the crude esterified product of Example 26 (i.e., 1.5 parts by weight of a hydrocarbon solvent was added with respect to 100 parts by weight of the crude esterified product). Then, a 10% potassium hydroxide aqueous solution containing an amount of potassium hydroxide that corresponds to 1.5 equivalents of the acid value of the crude esterified product was added thereto, and the mixture was stirred at 90° C. for 30 minutes. Although the mixture was allowed to stand for 30 minutes, the mixture was not separated into an ester layer and an alkali aqueous layer, and the entire mixture was in an emulsion state, and the aqueous layer could not be removed. Then, 200 g of 10% sodium sulfate hot water solution were added, and the mixture was stirred at 90° C. for 30 minutes and then allowed to stand for 30 minutes, followed by removal of the aqueous layer. Then, ion exchanged water was added in an amount of 20 parts by weight with respect to 100 parts by weight of the crude esterified product, and the mixture was stirred at 90° C. for 30 minutes and then allowed to stand for 30 minutes, followed by removal of the aqueous layer. This water washing process was repeated four times until the pH of the waste water became neutral. Then, the solvent in the ester layer was removed by distillation under a reduced pressure of 1 kPa at 180° C. Then, an adsorption process was performed by adding 5 g of Galleon Earth V2 (manufactured by Mizusawa Chemical Industries) and 5 g of Tomita AD300P (manufactured by Tomita Pharmaceutical Co. Ltd.). The temperature, the pressure and the time during the adsorption process were 100° C., 1 kPa and three hours, respectively. Then, the resultant mixture was filtrated. Thus, an ester having a kinematic viscosity (40° C.) of 104.8 mm$^2$/s, a pour point of −20° C., an acid value of 0.01 mgKOH/g, a hydroxyl value of 0.8 mgKOH/g, and a color number (APHA) of 60 was obtained in an amount of 926.0 g, as a final product. The yield of the ester with respect to the crude esterified product that was subjected to the neutralization treatment was 92.6%.

Example 27

First, 750.0 g (5.77 mol) of 2-ethylhexanol and 1556.5 g (5.48 mol) of stearic acid were put in a 3 liter four-necked flask provided with a thermometer, a nitrogen inlet tube, a stirrer and a condenser, and a reaction was conducted at atmospheric pressure under a nitrogen stream at 220° C. for 10 hours while removing water that was produced by the reaction by distillation. After the reaction was stopped, unreacted alcohol was removed by distillation under a reduced pressure of 1 kPa. Thus, a crude esterified product was obtained in an amount of 2144.1 g, and the acid value thereof was 0.8 mgKOH/g.

Then, 100 g of toluene and 100 g of isopropanol were added to 1000.0 g of the crude esterified product (i.e., 10 parts by weight of a hydrocarbon solvent and 10 parts by weight of an alcohol solvent were added with respect to 100 parts by weight of the crude esterified product). Then, a 10% potassium hydroxide aqueous solution containing an amount of potassium hydroxide that corresponds to 1.5 equivalents of the acid value of this crude esterified product was added thereto, and the mixture was stirred at 70° C. for 30 minutes. This mixture was allowed to stand for 30 minutes and the aqueous layer was removed, and thus a neutralization process was completed. Then, ion exchanged water was added in an amount of 20 parts by weight with respect to 100 parts by weight of the crude esterified product, and the mixture was stirred at 70° C. for 30 minutes and then allowed to stand for 30 minutes, followed by removal of the aqueous layer. This water washing process was repeated four times until the pH of the waste water became neutral. Then, the solvent in the ester layer was removed by distillation under a reduced pressure of 1 kPa at 180° C. Then, the obtained ester was distilled at 200° C., a pressure in the range of 10 to 500 Pa, and a flow rate of 4 mL/min with a Smith type distillatory. Thus, an ester having a kinematic viscosity (40° C.) of 9.7 mm$^2$/s, a pour point of 5.0° C., an acid value of 0.1 mgKOH/g, a hydroxyl value of 0.1 mgKOH/g, and a color number (APHA) of 30 was obtained in an amount of 825.2 g, as a final product. The yield of the ester with respect to the crude esterified product that had been subjected to the neutralization treatment was 82.5%.

Comparative Example 27

First, 1000.0 g of the crude esterified product of Example 27 was distilled at 200° C., a pressure in the range of 10 to 500 Pa, and a flow rate of 4 mL/min with a Smith type distillatory. Thus, an ester having a kinematic viscosity (40° C.) of 7.4 mm$^2$/s, a kinematic viscosity (40° C.) of 9.7 mm²/s, a pour point of 5.0° C., an acid value of 0.1 mgKOH/g, a hydroxyl value of 0.1 mgKOH/g, and a color number (APHA) of 80 was obtained in an amount of 764.2 g, as a final product. The yield of the ester with respect to the crude esterified product that had been subjected to the neutralization treatment was 76.4%.

Example 28

First, 750.0 g (5.77 mol) of 2-ethylhexanol and 1556.5 g (5.48 mol) of stearic acid were put in a 3 liter four-necked flask provided with a thermometer, a nitrogen inlet tube, a stirrer and a condenser, and a reaction was conducted at atmospheric pressure under a nitrogen stream at 220° C. for 10 hours while removing water that was produced by the reaction by distillation. After the reaction wag stopped, unreacted alcohol was removed by distillation under a reduced pressure of 1 kPa. Thus, a crude esterified product was obtained in an amount of 2144.1 g, and the acid value thereof was 0.8 mgKOH/g.

Then, 100 g of toluene and 100 g of isopropanol were added to 1000.0 g of the crude esterified product (i.e., 10 parts by weight of a hydrocarbon solvent and 10 parts by weight of an alcohol solvent were added with respect to 100 parts by weight of the crude esterified product). Then, a 10% potassium hydroxide aqueous solution containing an amount of potassium hydroxide that corresponds to 1.5 equivalents of the acid value of this crude esterified product was added thereto, and the mixture was stirred at 70° C. for 30 minutes. This mixture was allowed to stand for 30 minutes and the aqueous layer was removed, and thus a neutralization process was completed. Then, ion exchanged water was added in an amount of 20 parts by weight with respect to 100 parts by weight of the crude esterified product, and the mixture was stirred at 70° C. for 30 minutes and then allowed to stand for 30 minutes, followed by removal of the aqueous layer. This water washing process was repeated four times. Then, the solvent in the ester layer was removed by distillation under a reduced pressure of 1 kPa at 180° C. Then, an adsorption process was performed by adding 5 g of activated clay SA-1 (manufactured by Nihon Kassei Hakudo) and 5 g of activated alumina DN-1A (manufactured by Mizusawa Chemical Industries). The temperature, the pressure and the time during the adsorption process were 100° C., 1 kPa and three hours, respectively. Then, the resultant mixture was filtrated. Thus, an ester having a kinematic viscosity (40° C.) of 9.7 mm²/s, a pour point of 5.0° C., an acid value of 0.1 mgKOH/g, a hydroxyl value of 0.1 mgKOH/g, and a color number (APHA) of 40 was obtained in an amount of 934.3 g, as a final product. The yield of the ester with respect to the crude esterified product that was subjected to the neutralization treatment was 93.4%.

Comparative Example 28

An adsorption process was performed by adding 5 g of activated clay SA-1 (manufactured by Nihon Kassei Hakudo) and 5 g of activated alumina DN-1A (manufactured by Mizusawa Chemical Industries) to 1000.0 g of the crude esterified product of Example 28. The temperature, the pressure and the time during the adsorption process were 100° C., 1 kPa and three hours, respectively. Then, the resultant mixture was filtrated. Thus, an ester having a kinematic viscosity (40° C.) of 9.6 mm²/s, a pour point of 5.0° C., an acid value of 0.7 mgKOH/g, a hydroxyl value of 0.1 mgKOH/g, and a color number (APHA) of 90 was obtained in an amount of.968.2 g, as a final product. The yield of the ester with respect to the crude esterified product that was subjected to the neutralization treatment was 96.8%.

Tables 4 to 6 below shows the results of Examples 15 to 28 and Comparative Examples 15 to 28. In Tables 4 to 6, "Separation" shows the state of the separation of an ester layer and an aqueous layer at the time of the neutralization treatment. "◯" means that the separation is satisfactory, and emulsification did not occur. "×" means that the separation is poor, or emulsification occurred. "Δ" means that an emulsified layer was formed between an oil layer and an aqueous layer, and the separation of the layers was poor.

TABLE 4

| | | | | Properties of esters | | | |
|---|---|---|---|---|---|---|---|
| | Materials | Solvent[a] (parts by weight)[b] | Separation | Yield (%) | Kinematic viscosity at 40° C. (mm²/s) | Acid value (mgKOH/g) | APHA color number | Adsorbent |
| Example 15 | Trimethylolpropane Oleic acid | Toluene(20) Isopropanol(15) | ◯ | 91.2 | 64.2 | 0.11 | 190 | Galleon Earth V2 Tomita AD300P |
| Com. Ex. 15 | Trimethylolpropane Oleic acid | 20% Sodium sulfate | × | 76.1 | 64.1 | 0.20 | 450 | Galleon Earth V2 Tomita AD300P |
| Example 16 | Trimethylolpropane Caprylic acid | Toluene(15) | ◯ | 91.5 | 16.7 | 0.12 | 50 | Activated carbon Shirasagi C |
| Com. Ex. 16 | Trimethylolpropane Caprylic acid | — | Δ | 90.1 | 16.7 | 0.16 | 60 | Activated carbon Shirasagi C |
| Example 17 | Trimethylolpropane Oleic acid, Dimer acid | n-Heptane(10) | ◯ | 93.4 | 540.6 | 0.6 | 210 | Kyowaad 500SH |
| Com. Ex. 17 | Trimethylolpropane Oleic acid, Dimer acid | — | — | 98.9 | 521.2 | 3.6 | 300 | Kyowaad 500SH |
| Example 18 | Trimethylolpropane Caprylic acid, Capric acid Adipic acid | Xylene(20) Ethanol(5) | ◯ | 94.3 | 245.1 | 0.5 | 80 | — |
| Com. Ex. 18 | Trimethylolpropane Caprylic acid, Capric acid Adipic acid | Xylene(2) 10% Sodium sulfate | Δ | 91.9 | 240.0 | 0.8 | 100 | — |
| Example 19 | Dipentaerythritol 2-Ethylhexanoic acid 3,5,5-Trimethylhexanoic acid | Toluene(10) | ◯ | 92.6 | 227.6 | 0.01 | 90 | Activated clay SA-1 Activated alumina DN-1 |

TABLE 4-continued

| | Materials | Solvent[a] (parts by weight)[b] | Separation | Yield (%) | Kinematic viscosity at 40° C. (mm²/s) | Acid value (mgKOH/g) | APHA color number | Adsorbent |
|---|---|---|---|---|---|---|---|---|
| Com. Ex. 19 | Dipentaerythritol 2-Ethylhexanoic acid 3,5,5-Trimethylhexanoic acid | Toluene(2) | Δ | 88.4 | 227.1 | 0.01 | 150 | Activated clay SA-1 Activated alumina DN-1 |

[a]Solvent used for neutralization
[b]Parts by weight per 100 parts by weight of crude esterified product

TABLE 5

| | Materials | Solvent[a] (parts by weight)[b] | Separation | Yield (%) | Kinematic viscosity at 40° C. (mm²/s) | Acid value (mgKOH/g) | APHA color number | Adsorbent |
|---|---|---|---|---|---|---|---|---|
| Example 20 | Dipentaerythritol 2-Ethylhexanoic acid | Toluene(20) | ○ | 94.9 | 143.6 | 0.01 | 60 | Galleon Earth V2 Tomita AD300P |
| Com. Ex. 20 | Dipentaerythritol 2-Ethylhexanoic acid | Toluene(2.5) 10% Sodium sulfate | X | 86.3 | 143.6 | 0.01 | 120 | Galleon Earth V2 Tomita AD300P |
| Example 21 | Neopentylglycol n-Heptanoic acid Adipic acid | Xylene(20) | ○ | 95.7 | 267.5 | 0.01 | 30 | Galleon Earth V2 Tomita AD300P |
| Com. Ex. 21 | Neopentylglycol n-Heptanoic acid Adipic acid | 10% Sodium sulfate | X | 95.1 | 267.5 | 0.01 | 70 | Galleon Earth V2 Tomita AD300P |
| Example 22 | Neopentylglycol 2-Ethylhexanoic acid | Toluene(8) | ○ | 82.5 | 7.4 | 0.01 | 40 | — |
| Com. Ex. 22 | Neopentylglycol 2-Ethylhexanoic acid | — | Δ | 81.0 | 7.4 | 0.01 | 50 | — |
| Example 23 | Neopentylglycol 2-Ethylhexanoic acid | Toluene(8) | ○ | 93.5 | 7.4 | 0.01 | 50 | Kyowaad 500SH |
| Com. Ex. 23 | Neopentylglycol 2-Ethylhexanoic acid | — | Δ | 90.0 | 7.4 | 0.01 | 60 | Kyowaad 500SH |
| Example 24 | Pentaerythritol 2-Ethylhexanoic acid 3,5,5-Trimethylhexanoic acid | Toluene(10) | ○ | 92.5 | 69.2 | 0.01 | 40 | Kyowaad 500SH |
| Com. Ex. 24 | Pentaerythritol 2-Ethylhexanoic acid 3,5,5-Trimethylhexanoic acid | — | Δ | 91.2 | 69.2 | 0.01 | 60 | Kyowaad 500SH |

[a]Solvent used for neutralization
[b]Parts by weight per 100 parts by weight of crude esterified product

TABLE 6

| | Materials | Solvent[a] (parts by weight)[b] | Separation | Yield (%) | Kinematic viscosity at 40° C. (mm²/s) | Acid value (mgKOH/g) | APHA color number | Adsorbent |
|---|---|---|---|---|---|---|---|---|
| Example 25 | Pentaerythritol 2-Ethylhexanoic acid Caprylic acid, Capric acid | Cyclohexane(15) | ○ | 91.5 | 69.2 | 0.11 | 60 | Activated clay SA-1 Activated alumina DN-1 |
| Com. Ex. 25 | Pentaerythritol 2-Ethylhexanoic acid Caprylic acid, Capric acid | 10% Sodium sulfate | Δ | 90.4 | 33.4 | 0.15 | 70 | Activated clay SA-1 Activated alumina DN-1 |
| Example 26 | Pentaerythritol 3,5,5-Trimethylhexanoic acid | Toluene(10) | ○ | 95.5 | 104.8 | 0.01 | 35 | Galleon Earth V2 Tomita AD300P |
| Com. Ex. 26 | Pentaerythritol 3,5,5-Trimethylhexanoic acid | Toluene(1.5) 10% Sodium sulfate | X | 92.6 | 104.8 | 0.01 | 60 | Galleon Earth V2 Tomita AD300P |
| Example 27 | 2-Ethylhexanol Stearic acid | Toluene(10) Isopropanol(10) | ○ | 82.5 | 9.7 | 0.1 | 30 | — |
| Com. Ex. 27 | 2-Ethylhexanol Stearic acid | — | — | 76.4 | 9.7 | 0.1 | 80 | — |
| Example 28 | 2-Ethylhexanol Stearic acid | Toluene(10) Isopropanol(10) | ○ | 93.4 | 9.7 | 0.1 | 40 | Activated clay SA-1 Activated alumina DN-1 |

TABLE 6-continued

| | Materials | Solvent[a] (parts by weight)[b] | Separation | Yield (%) | Properties of esters | | | Adsorbent |
| | | | | | Kinematic viscosity at 40° C. (mm²/s) | Acid value (mgKOH/g) | APHA color number | |
|---|---|---|---|---|---|---|---|---|
| Com. Ex. 28 | 2-Ethylhexanol Stearic acid | — | — | 96.8 | 9.6 | 0.7 | 90 | Activated clay SA-1 Activated alumina DN-1 |

[a]Solvent used for neutralization
[b]Parts by weight per 100 parts by weight of crude esterified product In each of Examples 15 to 28, a good separation state was accomplished at the time of the neutralization treatment, and an ester having a low acid value and a satisfactory color number was obtained. On the other hand, in Comparative Examples 15 to 28, emulsification occurred at the time of the neutralization treatment, or an emulsified layer is formed between an oil layer and an aqueous layer, and thus the separation of the layers was poor.

Evaluation of Esters (Examples 19 to 24 and Comparative Examples 19 to 24)

Sealed tube tests are performed regarding the esters obtained in Examples 19 to 24 and Comparative Examples 19 to 24, and the thermal stability of the obtained esters was evaluated. Furthermore, in order to investigate conductive impurities dissolved in the esters, the volume resistivity of the esters was measured. The methods for these tests are shown below.

(a) Sealed Tube Test

Ten grams of an ester whose moisture content has been adjusted to 1,000 ppm, 5 g of hydrofluorocarbon R-407C (weight ratio of hydrofluorocarbon R-134a: hydrofluorocarbon R-125: hydrofluorocarbon R-32)=52:25:23), and pieces of iron, copper, and aluminum having a length of 10 mm were put in a glass tube, and the glass tube was sealed. This was heated at 175° C. for 14 days, and then the acid value and the color number (APHA) of the esters (esters for base stocks), were investigated and compared with those before heating.

(b) Electric Insulation Properties

The volume resistivity of the esters at 25° C. (JIS C2101) was measured.

Table 7 shows the measurement results of the above-described tests.

TABLE 7

| | (a) Sealed tube test | | | | (b) Volume resistivity ($\Omega \cdot cm$) |
| | Acid value (mgKOH/g) | | APHA color number | | |
| | Before heating | After heating | Before heating | After heating | |
|---|---|---|---|---|---|
| Example 19 | 0.01 | 0.02 | 90 | 100 | $6.4 \times 10^{14}$ |
| Com. Ex. 19 | 0.01 | 0.06 | 150 | 210 | $3.9 \times 10^{14}$ |
| Example 20 | 0.01 | 0.02 | 60 | 80 | $5.8 \times 10^{14}$ |
| Com. Ex. 20 | 0.01 | 0.12 | 120 | 190 | $3.3 \times 10^{12}$ |
| Example 21 | 0.01 | 1.2 | 30 | 90 | $2.6 \times 10^{13}$ |
| Com. Ex. 21 | 0.01 | 3.9 | 70 | 270 | $8.2 \times 10^{12}$ |
| Example 22 | 0.01 | 0.02 | 40 | 60 | $2.4 \times 10^{13}$ |
| Com. Ex. 22 | 0.01 | 0.03 | 50 | 70 | $1.1 \times 10^{13}$ |
| Example 23 | 0.01 | 0.5 | 50 | 70 | $2.2 \times 10^{13}$ |
| Com. Ex. 23 | 0.01 | 0.9 | 60 | 80 | $1.0 \times 10^{13}$ |

TABLE 7-continued

| | (a) Sealed tube test | | | | (b) Volume resistivity ($\Omega \cdot cm$) |
| | Acid value (mgKOH/g) | | APHA color number | | |
| | Before heating | After heating | Before heating | After heating | |
|---|---|---|---|---|---|
| Example 24 | 0.01 | 0.01 | 40 | 50 | $4.6 \times 10^{14}$ |
| Com. Ex. 24 | 0.01 | 0.08 | 60 | 100 | $2.3 \times 10^{14}$ |

The results of the sealed tube test indicate that in the esters of Examples 19 to 24, the increase of the acid value and the increase of the color number (APHA) after the tests were suppressed to be low, which indicates that they have excellent thermal stability. Furthermore, the high volume resistivities of the esters indicate that the contents of the conductive impurities in the esters are small.

Industrial Applicability

According to the method for producing esters of the present invention, crude esterified products obtained by a reaction of an alcohol and a carboxylic acid can be neutralized without causing poor separation of the layers or emulsification, and thus, high-quality esters can be produced with high yield.

The production method of the present invention is used to produce various types of esters. For example, a wax ester having a high melting point obtained by the present invention has a small content a low volatile substance and sharp melting characteristics, so that it can be used effectively, for example, as a releasing agent for toner. Highly viscous esters that are liquid at room temperature obtained by the present invention have excellent thermal stability and electric insulation properties. Such highly viscous esters can be used in applications where high levels of thermal stability and electric insulation properties are required, for example, as lubricants for refrigerating machine oil and special grease.

What is claimed is:

1. A method for producing an ester comprising:
   reacting an alcohol with a carboxylic acid to obtain a crude esterified product; and
   adding a hydrocarbon solvent to the crude esterified product and performing neutralization using an alkali aqueous solution,
   wherein the hydrocarbon solvent is at least one selected from the group consisting of toluene, xylene, an cyclohexane, and
   wherein the total amount of the hydrocarbon solvent added to the crude esterified product is 5 to 60 parts by weight with respect to 100 parts by weight of the crude esterified product.

2. The method for producing an ester according to claim 1, wherein in addition to the hydrocarbon solvent, a solvent that is an alcohol having 1 to 3 carbon atoms is further added to the crude esterified product in a ratio of 3 to 30 parts by weight with respect to 100 parts by weight of the crude esterified product, and then the neutralization is performed using an alkali aqueous solution.

3. The method for producing an ester according to claim 1, wherein the melting point of the ester is 50 to 100° C.

4. The method for producing an ester according to claim 1, wherein the kinematic viscosity of the ester at 40° C. is 60 to 50,000 mm$^2$/s.

5. The method for producing an ester according to claim 2, wherein th melting point of the ester is 50 to 100° C.

6. The method for producing an ester according to claim 2, wherein the kinematic viscosity of the ester at 40° C. is 60 to 50,000 mm$^2$/s.

* * * * *

UNITED STATES PATENT AND TRADEMARK OFFICE
CERTIFICATE OF CORRECTION

PATENT NO. : 6,939,980 B2
DATED : September 6, 2005
INVENTOR(S) : Memita et al.

It is certified that error appears in the above-identified patent and that said Letters Patent is hereby corrected as shown below:

<u>Column 42,</u>
Line 60, "xylene, an" should read -- xylene, and --.

<u>Column 44,</u>
Line 2, "th melting point" should read -- the melting point --.

Signed and Sealed this

Seventh Day of February, 2006

JON W. DUDAS
*Director of the United States Patent and Trademark Office*